US012320646B2

(12) United States Patent
Xu et al.

(10) Patent No.: US 12,320,646 B2
(45) Date of Patent: Jun. 3, 2025

(54) SYSTEMS, METHOD AND DEVICES FOR ASSISTING OR PERFORMING GUIDING INTERVENTIONAL PROCEDURES USING INERTIAL MEASUREMENT UNITS AND MAGNETOMETER SENSORS

(71) Applicants: Sheng Xu, Rockville, MD (US); Bradford J. Wood, Bethesda, MD (US); Tsz Ho Tse, Marietta, GA (US); The United States of America, as represented by the Secretary, Department of Health & Human Services, Rockville, MD (US)

(72) Inventors: Sheng Xu, Rockville, MD (US); Bradford J. Wood, Bethesda, MD (US); Tsz Ho Tse, Marietta, GA (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 325 days.

(21) Appl. No.: 16/613,591

(22) PCT Filed: May 16, 2018

(86) PCT No.: PCT/US2018/033025
§ 371 (c)(1),
(2) Date: Nov. 14, 2019

(87) PCT Pub. No.: WO2018/213489
PCT Pub. Date: Nov. 22, 2018

(65) Prior Publication Data
US 2020/0197099 A1  Jun. 25, 2020

Related U.S. Application Data

(60) Provisional application No. 62/506,872, filed on May 16, 2017.

(51) Int. Cl.
*A61B 5/00* (2006.01)
*A61B 34/00* (2016.01)
(Continued)

(52) U.S. Cl.
CPC .............. *G01C 21/16* (2013.01); *A61B 34/20* (2016.02); *A61B 34/25* (2016.02);
(Continued)

(58) Field of Classification Search
CPC .... A61B 2034/2048; A61B 2034/2072; A61B 90/11; A61B 2017/3413
See application file for complete search history.

(56) References Cited

U.S. PATENT DOCUMENTS 5,281,149 A * 1/1994 Petri ...................... H05K 7/142
439/74
7,837,627 B1 * 11/2010 Pruter .................... A61B 46/10
604/117
(Continued)

FOREIGN PATENT DOCUMENTS

KR  20170030687 A  3/2017
WO  2016/154442 A1  9/2016

OTHER PUBLICATIONS

International Search Report issued in PCT/US2018/033025, dated Sep. 6, 2018.

*Primary Examiner* — Rajeev P Siripurapu
(74) *Attorney, Agent, or Firm* — Leydig, Voit & Mayer, Ltd.

(57) ABSTRACT

An instrument tracker includes a case having an interior and exterior with a plurality of instrument seats, an inertial measurement unit (IMU), and a controller. The IMU and controller are arranged within the interior of the case and the controller is disposed in communication with the IMU and is responsive to instructions recorded on a memory to
(Continued)

receive position information from the IMU, determine at least one of position and orientation of an instrument fixed relative to the case by the plurality of instrument seats using the position information received from the IMU, and transmit the at least one of position and orientation to a display device for displaying position and orientation of the instrument relative to a predetermined insertion path through a subject between an entry point on the surface of the subject and a region of interest within the interior of the subject. Instrument tracking systems and methods tracking position of instruments are also described.

17 Claims, 26 Drawing Sheets

(51) Int. Cl.
*A61B 34/20* (2016.01)
*G01C 21/16* (2006.01)
*A61B 90/00* (2016.01)

(52) U.S. Cl.
CPC .. *G01C 21/1654* (2020.08); *A61B 2034/2048* (2016.02); *A61B 2034/2051* (2016.02); *A61B 2034/2072* (2016.02); *A61B 2034/2074* (2016.02); *A61B 2090/062* (2016.02); *A61B 2090/067* (2016.02); *A61B 2560/0214* (2013.01)

(56) References Cited

U.S. PATENT DOCUMENTS

| | | | |
|---|---|---|---|
| 2006/0004286 A1* | 1/2006 | Chang | A61B 90/16 606/198 |
| 2011/0066160 A1 | 3/2011 | Simaan et al. | |
| 2014/0135616 A1* | 5/2014 | Stein | A61B 17/92 600/424 |
| 2014/0257196 A1 | 9/2014 | Gobron et al. | |
| 2015/0327885 A1* | 11/2015 | Esanu | A61B 17/3439 606/192 |
| 2016/0278746 A1* | 9/2016 | Hancu | A61B 5/4312 |
| 2016/0296179 A1* | 10/2016 | Thompson | A61B 17/3403 |
| 2017/0172458 A1* | 6/2017 | Kato | A61B 5/1128 |

* cited by examiner

- Gyroscope
- Gravity Sensor
- Bluetooth
- Battery

SYSTEMS, METHOD AND DEVICES FOR ASSISTING OR PERFORMING GUIDING INTERVENTIONAL PROCEDURES USING INERTIAL MEASUREMENT UNITS AND MAGNETOMETER SENSORS

CROSS REFERENCE TO RELATED APPLICATIONS

This application is a U.S. National Phase Application filed under 35 U.S.C. § 371, based on International PCT Patent Application No. PCT/US2018/033025, filed May 16, 2018, which application claims the benefit of U.S. Provisional Application Ser. No. 62/506,872, filed May 16, 2017, and entitled SYSTEMS, METHOD AND DEVICES FOR ASSISTING OR PERFORMING GUIDING INTERVENTIONAL PROCEDURES USING INERTIAL MEASUREMENT UNITS AND MAGNETOMETER SENSORS, the contents of each of which is incorporated herein by reference in its entirety.

BACKGROUND OF THE INVENTION

1. Field of the Invention

The present disclosure is directed to interventional procedures, and more particularly to a guided interventional procedures using instrument-mounted inertial measurement units.

2. Description of Related Art

Intervention procedures, such as computed tomography intervention procedures, are commonly used to deliver therapy to a targeted region of the subject undergoing the intervention procedure. Intervention procedures generally entail inserting a needle into the subject and advancing the needle into the subject to the targeted region and delivering a selected therapy. Examples of therapies include ablation, etc. Needle orientation and position is typically done freehand, i.e., by relying on the skill of a surgeon in manipulating the needle during advancement, to avoid damaging structures along the needle advancement path.

Various techniques are known to control accuracy of needle positioning during freehand needle insertions. For example, robotic-assisted, cone beam computed tomography, laser guidance, optical tracking, electromagnetic tracking, fused modality imaging have all been used to improve needle accuracy during needle insertions in intervention procedures. Robotic systems with guidance systems have been employed in microwave thermoablation intervention procedures. Cone beam computed tomography has been used to reduce tip to target error between the needle and target in certain intervention procedures. Laser guidance systems have been used track needle position during other intervention procedures. Optical tracking systems, generally employing cameras and tracking markers emplaced on the subject have been used in still other intervention procedures. Electromagnetic tracking, which utilizes the electromagnetic properties of the need for tracking, has been used to improve needle positioning accuracy in other intervention procedures. Modality fusion techniques, where imaging information from more than imaging modality as fused to provide an image using date from the more than one imaging modality, have been used in still other intervention procedures to improve needle position accuracy.

While generally satisfactory for their intended purpose the known methods of needle position monitoring each have limitations that can limit the application of the technique. For example, robotic systems can bring added cost, complexity, and additional workflow to intervention procedures. Cone beam CT techniques can be limited to needle size. Laser guidance systems can impose requirements on the patient that are impractical, for example requiring the patient to remain motionless for extended periods of time. Optical tracking can require line of sight between the cameras and tracking markers on the instrument, imposing restrictions on movement during the intervention procedure. Electromagnetic tracking techniques can be frustrated by the presence of metal or magnetic objects in the vicinity of the needle. And mixed mode imaging techniques require registration of images using fiducial markers, which adds complexity sources error.

Such conventional methods and systems have generally been considered satisfactory for their intended purpose. However, there is still a need in the art for improved systems and methods for instrument tracking, visualizing, and monitoring during intervention procedures. The present disclosure provides a solution for this need.

SUMMARY OF THE INVENTION

An instrument tracker includes a case having an interior and exterior with a plurality of instrument seats, an inertial measurement unit (IMU) arranged within the interior of the case, and a controller. The controller is arranged within the interior of the case, is disposed in communication with the IMU, and is responsive to instructions recorded on a non-transitory machine readable medium to receive position information from the IMU and determine at least one of position and orientation of an instrument fixed relative to the case by the plurality of instrument seats using the position information received from the IMU. The instructions also cause the controller to transmit the at least one of position and orientation to a display device for displaying position and orientation of the instrument relative to a predetermined insertion path through a subject between an entry point on the surface of the subject and a region of interest within the interior of the subject.

In certain embodiments the case can include four supports arranged on the interior of the case to support the IMU. The plurality of instrument seats can define an instrument channel. The instrument channel can be substantially perpendicular to the case. The case can include a grip with a finger seat disposed on the exterior of the case. The finger seat can be disposed on the on a side of the grip opposite the plurality of instrument seats. The case can include a finger ring disposed on the exterior of the case. One of the plurality of instrument seats can be disposed on a side of the other of the plurality of instrument seats opposite the finger ring.

In accordance with certain embodiments the IMU can include one or more of a magnetometer, an accelerometer, and a gyroscope. The one or more of a magnetometer, an accelerometer, and a gyroscope can be disposed in communication with the controller. A battery can be battery arranged within the interior of the case end. The battery can be electrically connected to the IMU and the controller. A wired charging circuit can be electrically connected to the battery for direct-connect charging of the battery. A wireless charging circuit can be electrically connected to the battery for wirelessly charging of the battery. The instrument tracker can include a wireless communication module for communication with a display device. The controller can be operatively connected to the wireless communication module.

It is contemplated that an instrument can be received within the plurality of instrument seats and fixed relative to the case. The instrument can include a needle, a catheter, or a portable imaging device. The tracking instrument can include a tracker user interface. The tracker user interface can be fixed relative to the case. The controller can be operatively connected to the tracker user interface. The tracker user interface can include an auditory module and/or a display module. It is also contemplated that the region of interest can include an anatomical target of a subject undergoing an intervention procedure, such as a tumor.

In further embodiments a display device can be in wireless communication with the tracker controller. The display device can have a display device controller communicative with a display device memory. The display device memory can have instructions recorded on it that, when read by the display device controller, cause the display device controller to receive image data including the subject of interest, define a path to the subject of interest extending between an entry point located on a subject and a region of interest disposed within the subject, and receive data from the instrument tracker indicative of angular position and insertion depth of the instrument fixed relative to the tracker. The instructions can cause the display device to display the instrument angular position and/or insertion depth relative to the insertion path defined between the surfaced of the subject and the region of interest.

An instrument tracking system includes an instrument tracker as described above with a wireless communication module and a display device. The tracker controller is operatively connected to the wireless communication module for communicating at least one of angular orientation and insertion depth to the display device. The display device is in wireless communication with the tracker controller has a display device controller in communication with a memory. The memory has a non-transitory machine readable medium with instructions recorded on it that, when read by the display device controller, cause the display device controller to receive image data of the subject including a region of interest, define an insertion path to the region of interest extending between an entry point located on the surface of the subject and the region of interest, receive data from the instrument tracker indicative of at least one of angular position and insertion depth of an instrument received within the plurality of instrument seats on the case of the instrument tracker, and display the at least one of the instrument angular position and insertion depth relative to the insertion path defined to the region of interest located within the subject.

In certain embodiments the instrument tacking system includes an imaging device disposed in communication with the display device. The imaging device can include one or more of an x-ray imaging device, a computerized tomography device, a positron emission tomography imaging device. The imaging device can include one or more of a magnetic resonance imaging device, a ultrasound imaging device, and a fluoroscopic imaging device.

A method of tracking position of an instrument includes fixing an instrument tracker as described above to an instrument, receiving position information from the IMU, and determining at least one of angular orientation and insertion depth of the instrument using the position information received from the IMU. The at least one of the angular orientation and insertion depth of the instrument is transmitted to a display device disposed in communication with the instrument tracker, the at least one of angular orientation and insertion depth of the instrument compared to a predetermined instrument insertion path defined between an entry point, located on the subject, and the region of interest within the subject, and the difference between the at least one of angular orientation and insertion depth of the instrument to the instrument path displayed on the display device.

In certain embodiments the method can include imaging a subject including a region of interest located within the subject. The method can include determining the predetermined instrument insertion path using imaging data acquired during imaging of the subject. At least one of the angular orientation and the insertion depth of the instrument can be adjusted based on the comparison between the difference between the at least one of angular orientation and insertion depth of the instrument to the instrument path on a display device. Position of the instrument can be confirmed by imaging the instrument and the subject including the region of interest subsequent to completion of insertion of the instrument along the insertion path.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION OF THE PREFERRED EMBODIMENTS

Figure 1:
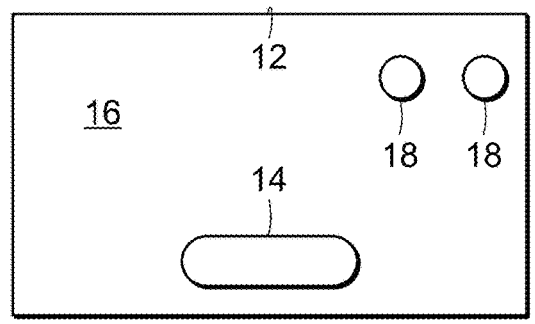
FIG. 1 is schematic view of a subject having a region of interest disposed within the interior of the subject, showing obstacles between the surface of the object and the region of interest.

Reference will now be made to the drawings wherein like reference numerals identify similar structural features or aspects of the subject disclosure. For purposes of explanation and illustration, and not limitation, a partial view of an exemplary embodiment of an instrument tracker in accordance with the disclosure is shown in FIG. 3 and is designated generally by reference character 100. Other embodiments of instrument trackers, instrument tracking systems, and methods of tracking instruments in accordance with the disclosure, or aspects thereof, are provided in FIGS. 1, 2 and 4-25B, as will be described. The systems and methods described herein can be used for tracking position of instruments during intervention procedures, such as needle position relative to a predetermined insertion during cancer treatments, though the present disclosure is not limited to cancer treatment interventions nor to needle positioning in general.

Referring to FIG. 1, a subject 10 is shown. Subject 10 has surface 12 with a region of interest 14 located within an interior 16 of subject 10. Subject 10 also has a plurality of obstacles 18 located within interior 16 between surface 12 and region of interest 14, obstacles 18 limiting the possible insertion paths to region of interest 14 from surface 12. In certain embodiments subject 10 is a patient, region of interest 14 is a tumor that is the subject of an intervention procedure entailing the insertion of an instrument 20 (shown in FIG. 4) into subject 10, and obstacles 18 are bony structures or blood vessels which are to be avoided when introducing instrument 20 into subject 10. Instrument 20 can include one or more of a needle, a catheter, and a portable imaging device, as suitable for an intended intervention procedure. It is contemplated that region of interest 14 include an anatomical target of subject 10 undergoing the intervention procedure, such as a tumor by way of non-limiting example.

Figure 2:
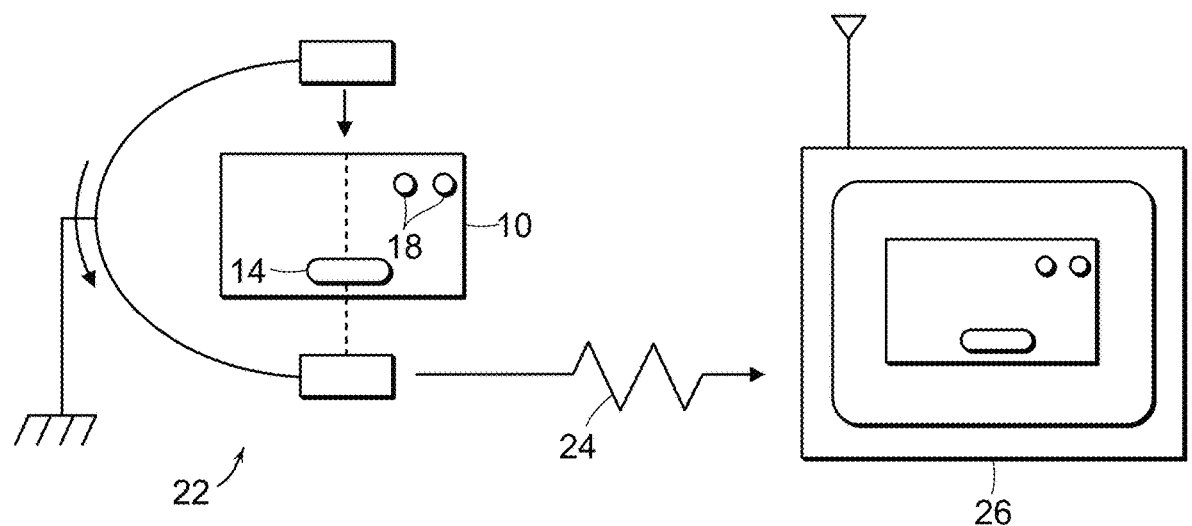
FIG. 2 is a schematic view of the subject of FIG. 1 undergoing imaging, showing image data from the imaging operation being reconstructed on a display device for viewing the region of interest and obstacles within the interior of the subject.
Figure 3:
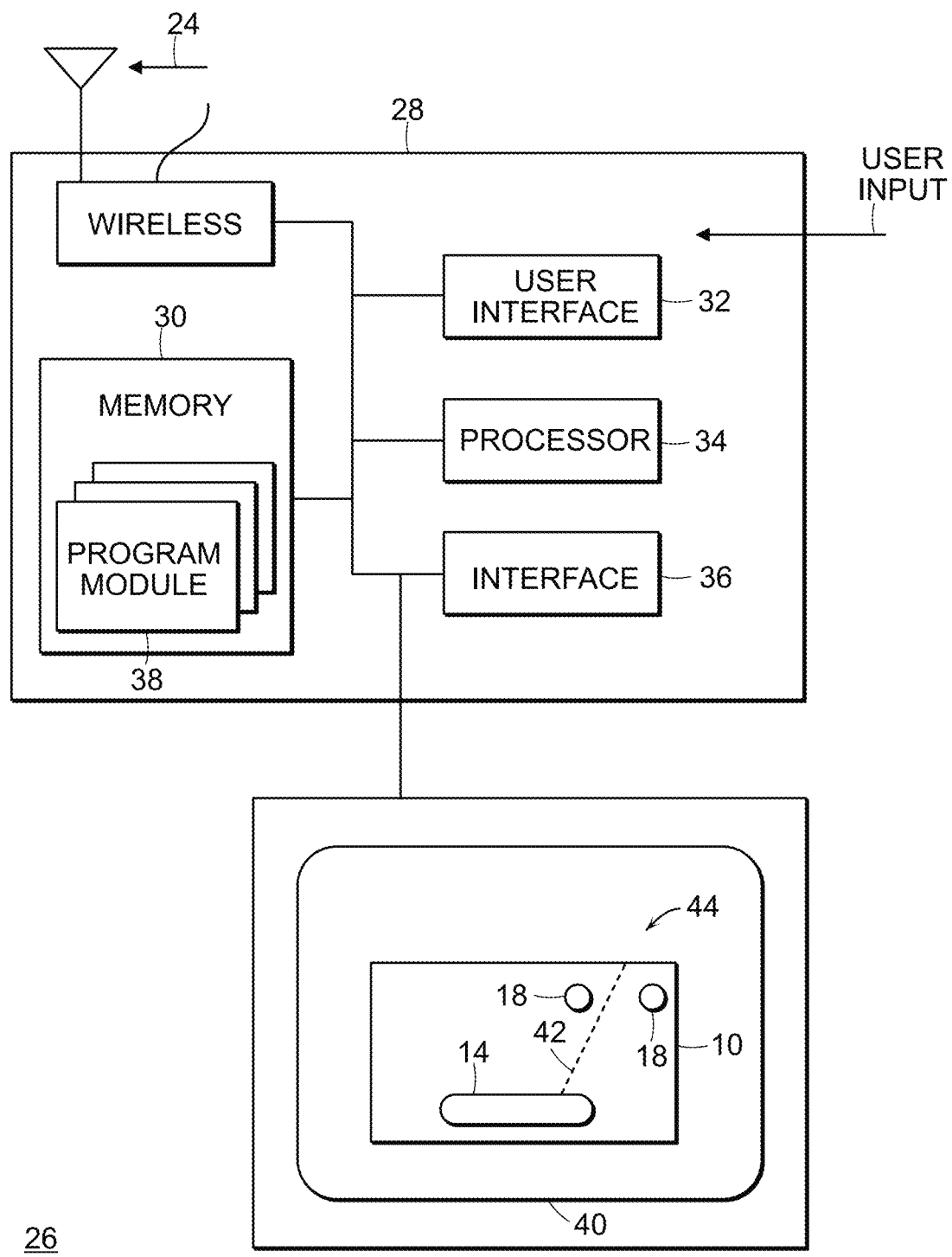
FIG. 3 is a schematic view of the display device of FIG. 2, showing elements of the display device including a processor and program modules for selecting an insertion path between an entry point on the surface and the region of interest within the interior of the subject.

With reference to FIG. 2, imaging subject 10 including region of interest 14 located within subject 10 is shown. Imaging subject 10 includes positioning subject 10 within an imaging device 22 and acquiring image data 24 including subject 10 and region of interest 14. Imaging data 24 is communicated using a communications link to a display device 26, which reconstructs an image of subject 10 include region of interest 14 and obstacles 18. It is contemplated that imaging device 22 can include one or more of an x-ray imaging device, a computerized tomography device, a positron emission tomography imaging device, a magnetic resonance imaging device, and a ultrasound imaging device disposed in communication with display device 26, as suitable for an intended application.

With reference to FIG. 3, display device 26 is shown. Display device 26 includes a display device controller 28, a memory 30, a user interface 32, a processor 34, and an interface 36. Processor 34 is disposed in communication with memory 30. Memory 30 includes a non-transitory machine readable medium having a plurality of program modules 38 recorded on memory 30. Program modules 38 include instructions that, when read by processor 34 cause processor 34 to undertake certain actions, e.g., a method 200 (shown in FIG. 21) of tracking position of an instrument.

Display device 26 receives image data 24 from imaging device 22 (shown in FIG. 2) and reconstructs an image 40 including subject 10. Further, using image data 24 and/or in conjunction with user input received at user interface 32, display device 26 generates an insertion path 42. Predetermined insertion path 42 extends between an entry point 44 surface 12 of subject 10 and region of interest 14. It is contemplated that predetermined insertion path 42 bypass obstacles 18 during an intervention procedure targeting region of interest 14, avoiding obstacles and/or collateral injury that otherwise could occur to obstacles 18 during insertion and/or intervention. This path planning, which can be coincident with imaging subject 10, results in the generation of a predetermined insertion path 42 between entry point 44 and region of interest 14. Although a single insertion path and region of interest are show in FIG. 3 those of skill in the art will appreciate that more than one insertion path and/or more than one region of interest 14 can exist within subject 10.

Figure 4:
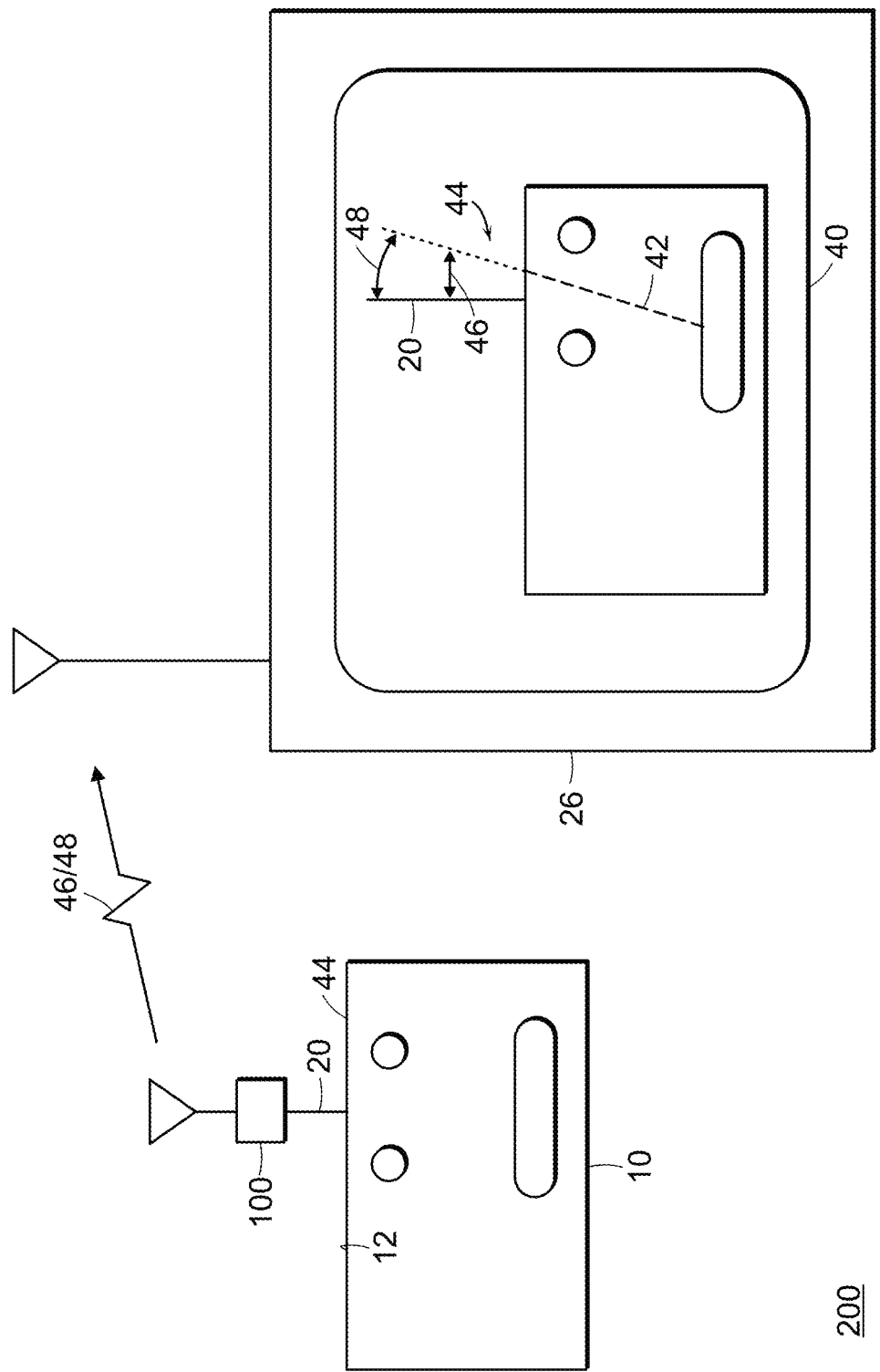
FIG. 4 is a schematic view of an instrument being located on the surface of the subject for performing an intervention therapy on the subject of FIG. 1, showing the instrument being registered with the entry point using tracking data communicate from an instrument tracker coupled to the instrument to the display device.
Figure 5:
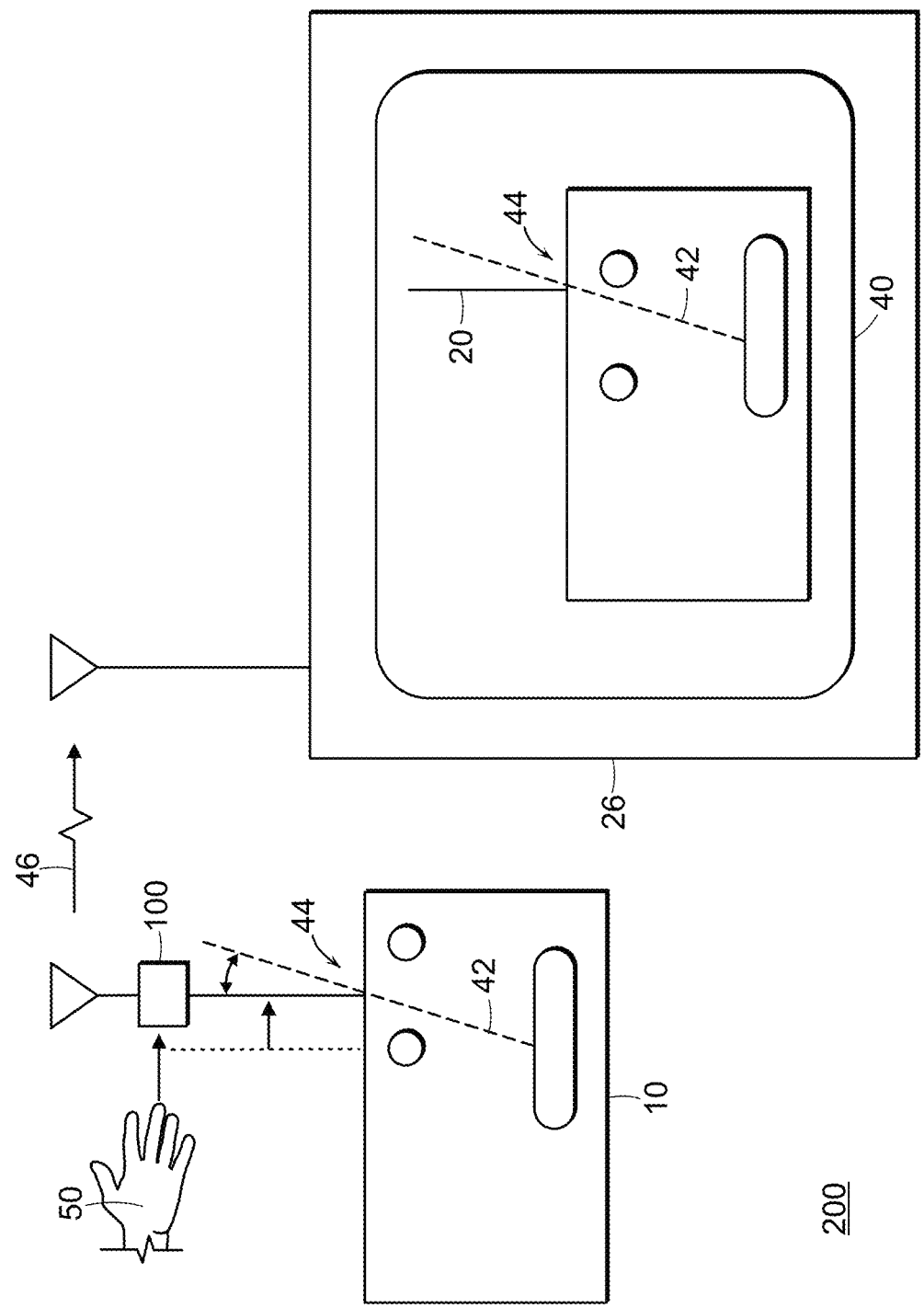
FIG. 5 is a schematic view of the subject of FIG. 1 undergoing the intervention therapy, showing a user re-positioning the instrument using position data communicated by the instrument tracker to the display device.
Figure 6:
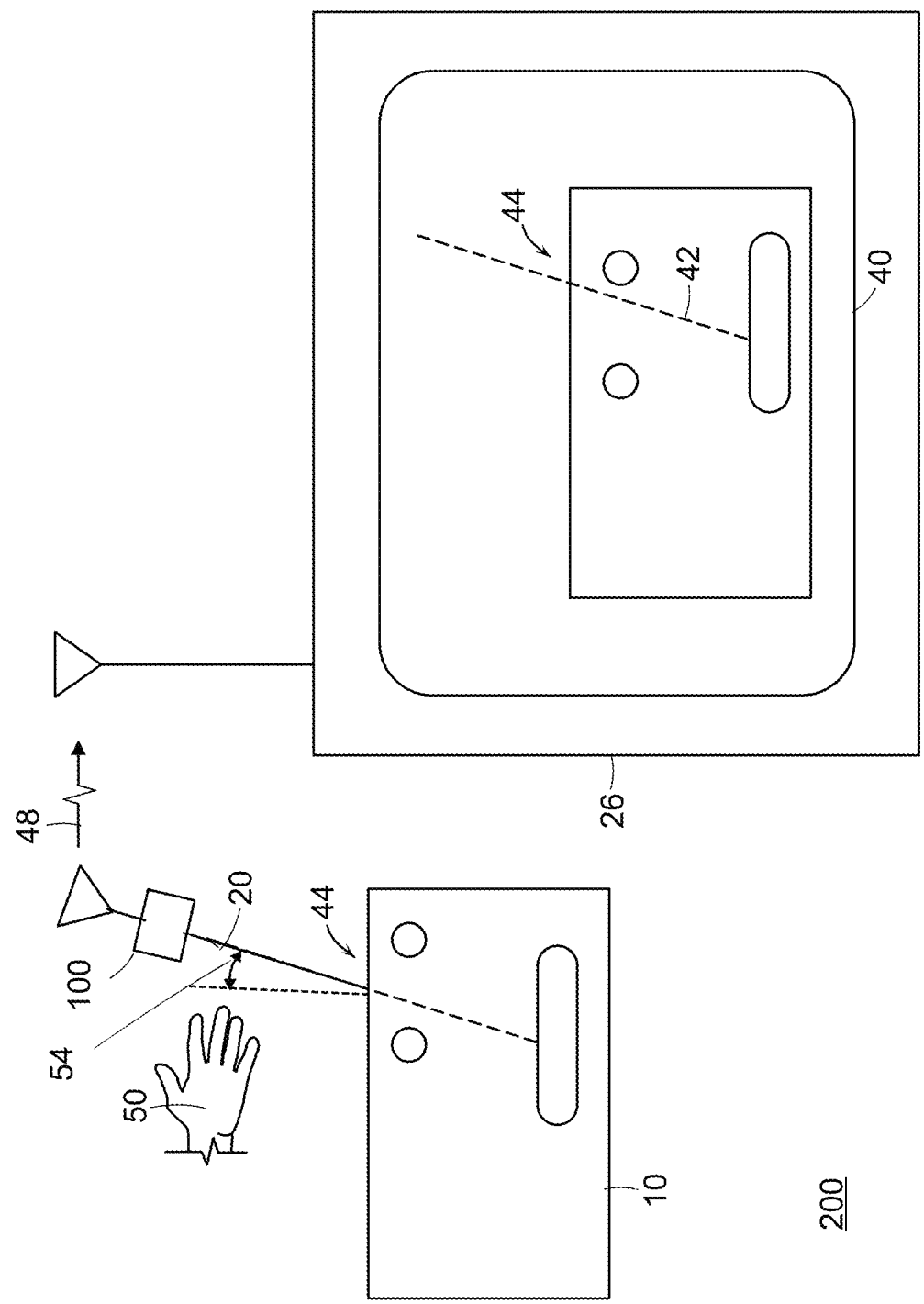
FIG. 6 is a schematic view of the subject of FIG. 1 undergoing the intervention therapy, showing the user re-orienting the instrument using orientation data communicated by the instrument tracker to the display device.

With reference to FIG. 4, instrument 20 is shown in an initial placement on surface 12 of subject 10. As is possible under some circumstances, the illustrated placement of instrument 20 is offset from the entry point 44. To visualize the relative position of instrument 20 relative to predetermined insertion path 42 instrument tracker 100 is removably fixed to instrument 20. Instrument tracker 100 is configured and adapted to transmit at least one of position information 46 and angular orientation information 48 of instrument 20 to display device 26. Display device 26 in turn displays at least one of position information 46 and angular orientation information 48 of instrument 20 relative to predetermined insertion path 42, thereby providing the user with real-time indication of registration (and/or registration error) of instrument 20 with predetermined insertion path 42 in image 40. It is contemplated that, based on display It is contemplated that, based on image 40 containing subject 10 and predetermined insertion path 42, that a user 50 adjust position of instrument 20 relative to subject 10. This is illustrated schematically in FIG. 5, wherein user 50 is shown adjusting 52 position of instrument 20 using tactile engagement of instrument tracker 100, and therethrough instrument 20, to register instrument 20 with entry point 44. It is also contemplated that, based on image 40 containing subject 10 and predetermined insertion path 42, that user 50 adjust angular orientation of instrument 20 relative to subject 10. This is illustrated schematically in FIG. 6, wherein user 50 is shown adjusting 54 position of instrument 20 using tactile engagement of instrument tracker 100, and therethrough instrument 20, to align instrument 20 with predetermined insertion path 42.

Figure 7:
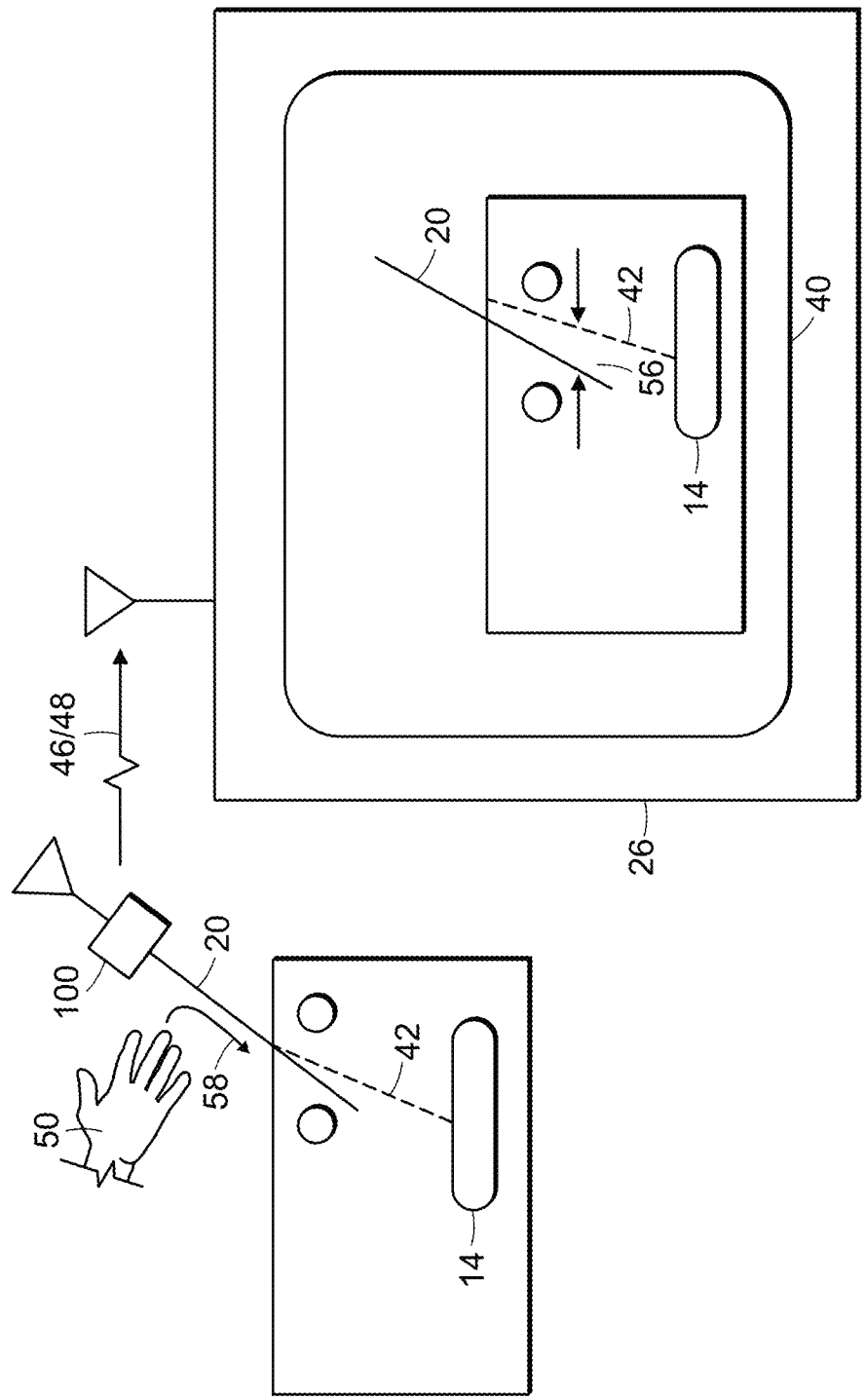
FIG. 7 is a schematic view of the subject of FIG. 1 undergoing the intervention therapy, showing the instrument being advanced along the insertion path by the user with the instrument position indicated in real-time on the display device using position and/or orientation data communicated by the instrument tracker to the display device.

With reference to FIG. 7, instrument 20 is shown being advanced into subject 10 along predetermined insertion path 42. Instrument 20 is advanced 58 along predetermined insertion path 42 by user 50 by tactile engagement with instrument tacker 100. This causes instrument 20 to approach region of interest 14 in the general direction of predetermined insertion path 42. Progress of instrument 20 through subject 10 is provided real time through at least one of position information 46 and angular orientation information 48 of instrument 20 relative to predetermined insertion path 42 communicated wireless by instrument tracker 100 to display device 26, which displays position and orientation of instrument 20 relative to predetermined insertion path 42 in image 40.

Figure 8:
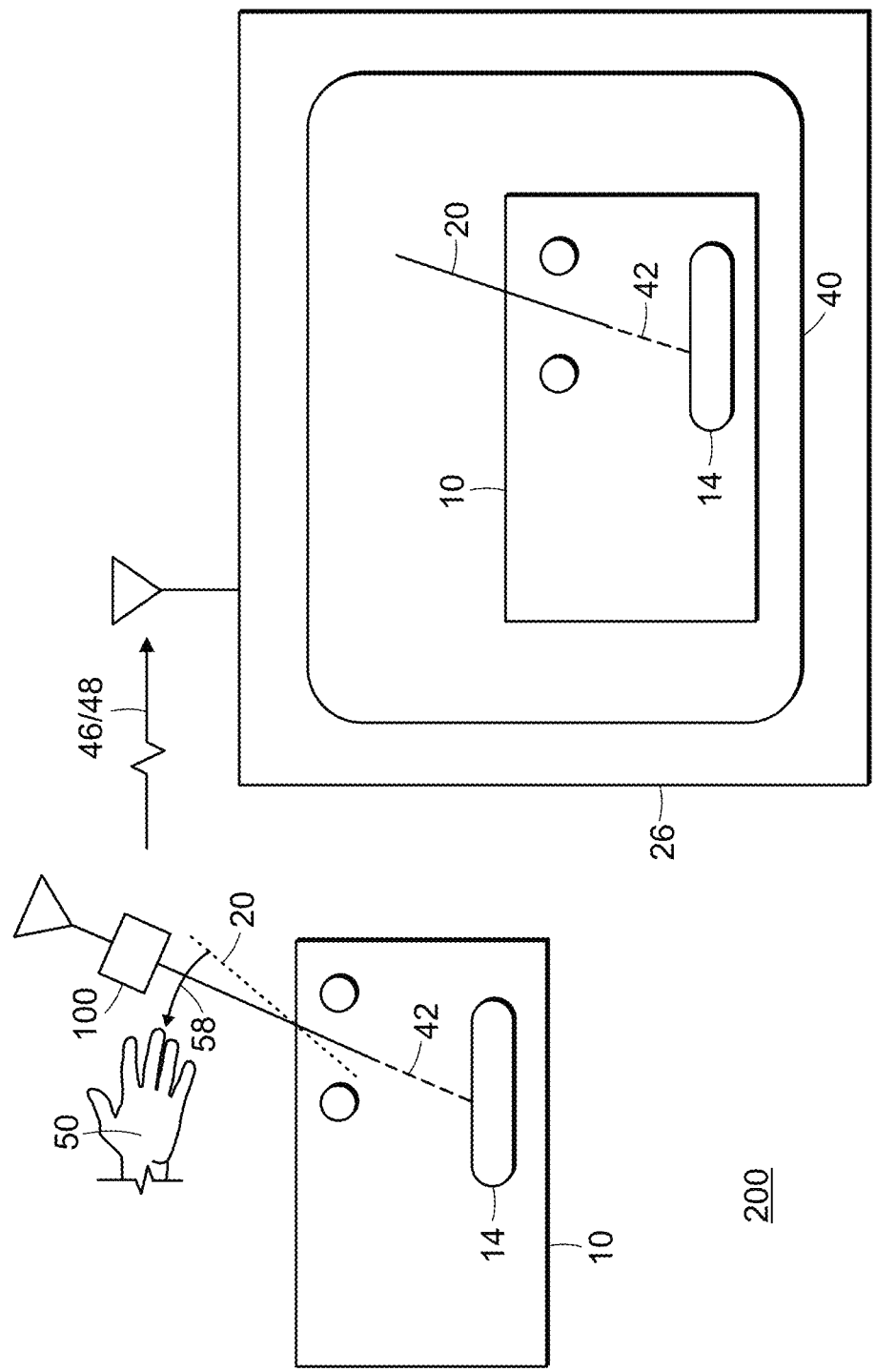
FIG. 8 is a schematic view of the subject of FIG. 1 undergoing the intervention therapy, showing the user making a correction to the instrument position relative to the insertion path during insertion based on the real time position and/or orientation data communicated by the instrument tracker to the display device.

As will be appreciated by those of skill in the art, position and/or orientation of instrument 20 can diverge from predetermined insertion path 42. Display device 26 displays divergence 56, which allows user to make one or more corrective adjustments 58 during insertion response to the at least one of position information 46 and angular orientation information 48 of instrument 20 relative to predetermined insertion path 42 presented in image 40 on display device 26. An exemplary corrective adjustment 58 is shown in FIG. 8, which shows instrument 20 aligned and registered to predetermined insertion path 42.

Figure 9:
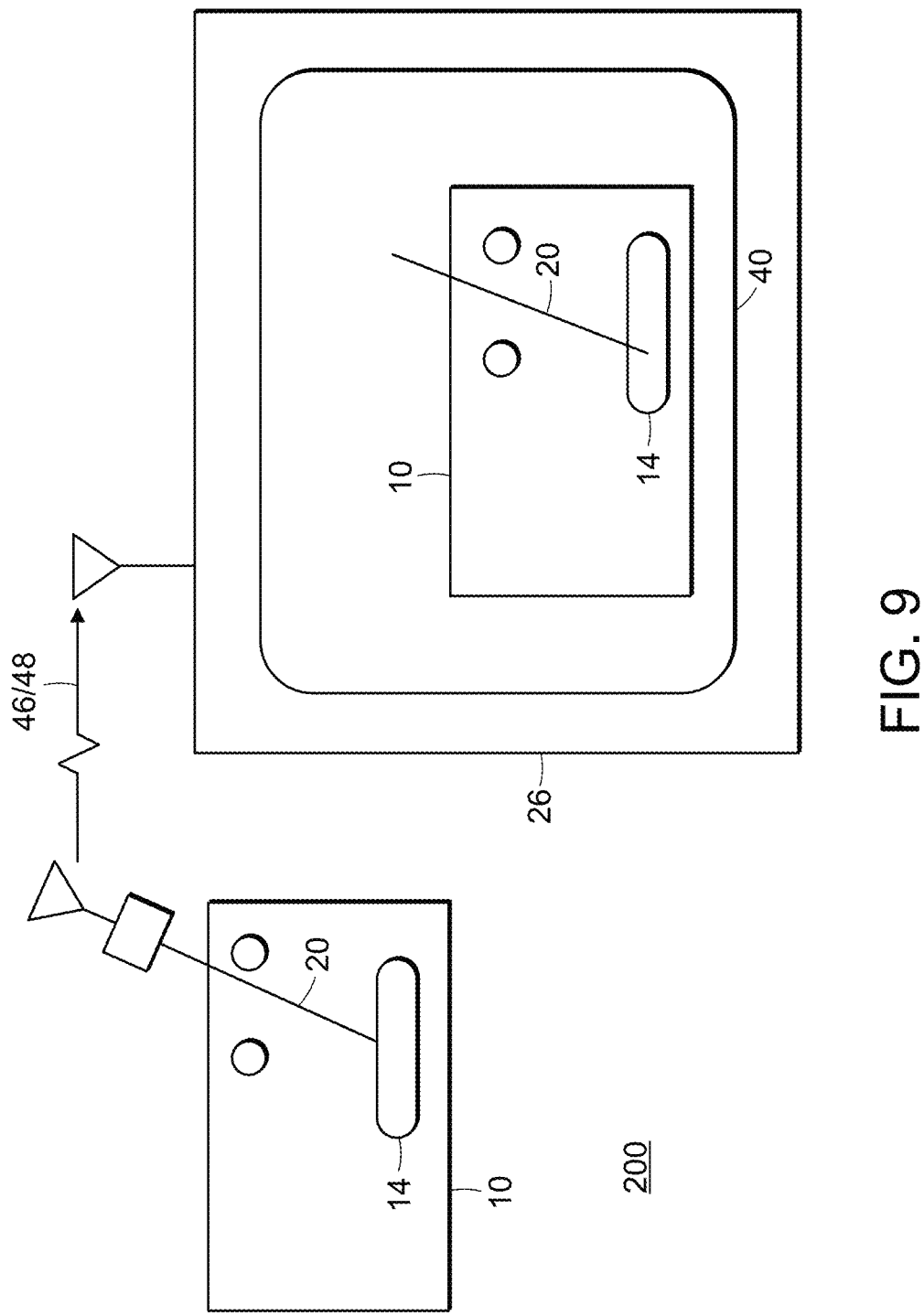
FIG. 9 is a schematic view of the subject of FIG. 1 undergoing the intervention therapy, showing the instrument received within the region of interest along the insertion path.
Figure 10:
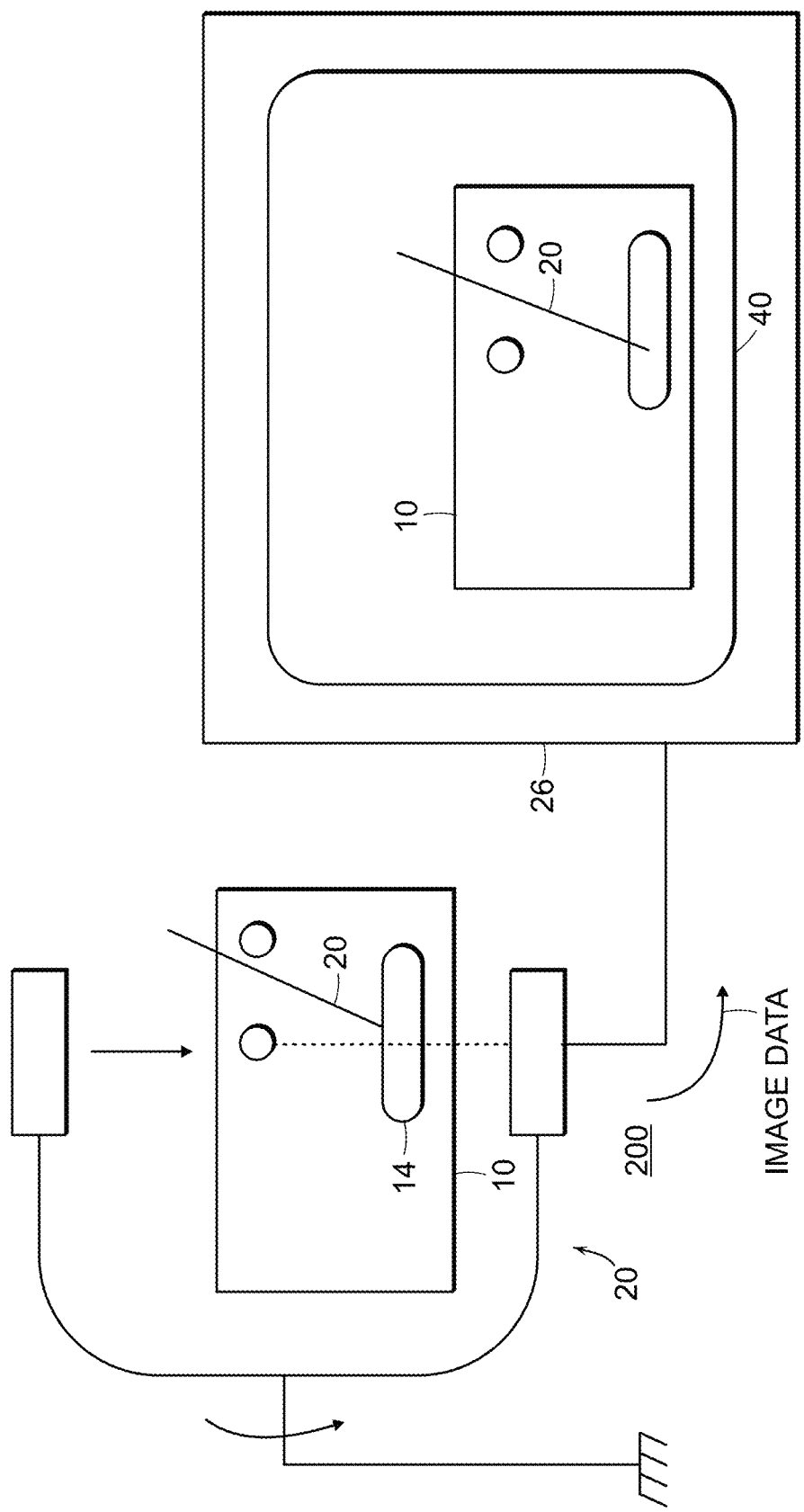
FIG. 10 is a schematic view of the subject of FIG. 1 undergoing the intervention therapy, showing the subject and instrument undergoing an imaging procedure to image the instrument and subject.

With reference to FIGS. 9 and 10, it is contemplated that user 50 advance instrument 20 along predetermined insertion path 42 using at least one of position information 46 and angular orientation information 48 of instrument 20 relative to predetermined insertion path 42 presented in image 40 until instrument 20 reaches region of interest 14. Subject 10 and instrument 20 are thereafter imaged using imaging device 22, optionally, to confirm the at least one of position information 46 and angular orientation information 48 of instrument 20 relative to predetermined insertion path 42 reported by instrument tracker 100 adequately represent the position and orientation of instrument 20 relative to region of interest 14 prior to proceeding with further steps in the selected intervention therapy.

Figure 11:
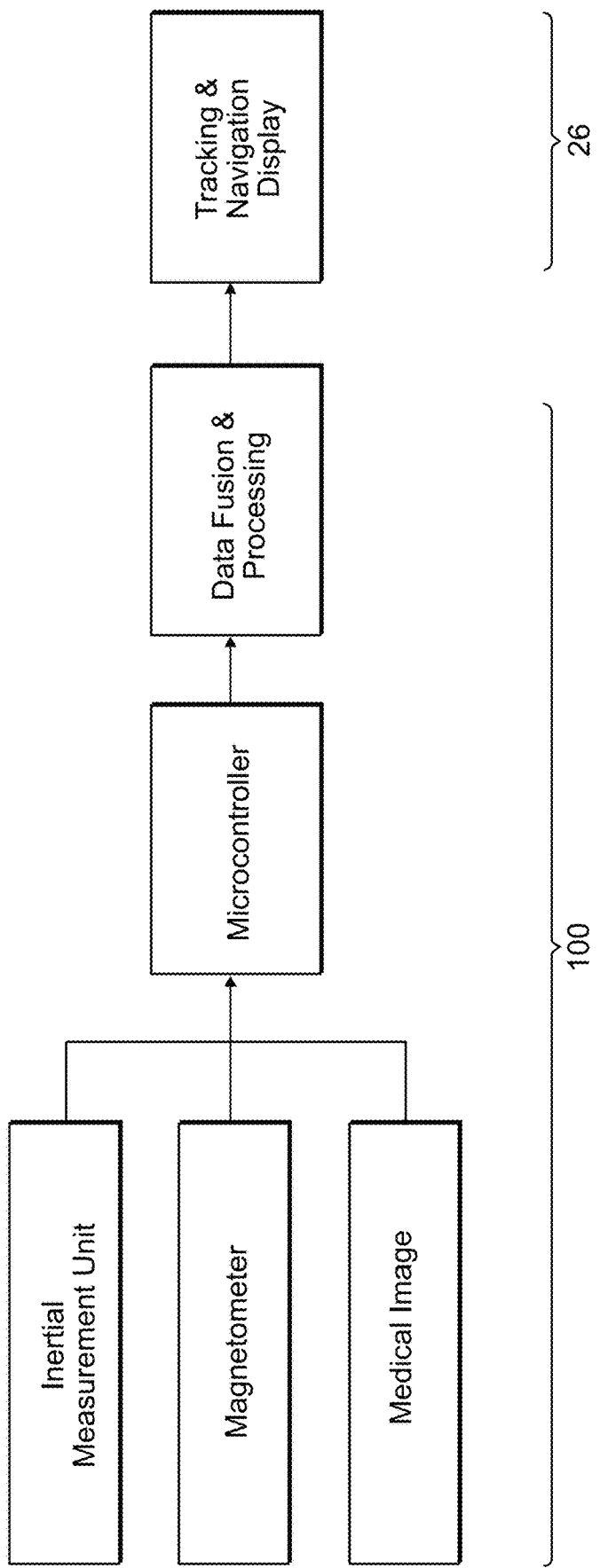
FIG. 11 is a schematic view of an instrument tracking system, functional blocks of an instrument tracker and a display module of the instrument tracking system.

With reference to FIG. 11, instrument tracking system 200 is shown. Instrument tracking system includes instrument tracker 100 (shown in FIG. 4) and display device 26 (shown in FIG. 3). Instrument tracker 100 includes a wireless communication module 108 (shown in FIG. 12) for wireless communication with display device 26 and controller 106 (shown in FIG. 12) operatively connected to wireless communication module 108 for communicating at least one of position information 46 (shown in FIG. 4) and angular orientation information 48 (shown in FIG. 4) of instrument tracker 100 to display device. Position information 46 and angular orientation information 48 are generated using position information controller 106 receives from IMU 104 (shown in FIG. 12), which can include magnetometer 134 (shown in FIG. 12). Controller 106 fuses the position information 46 and angular information 48 with image data 24 (shown in FIG. 2) of subject 10 (shown in FIG. 1) for display on display device 26.

Figure 12:
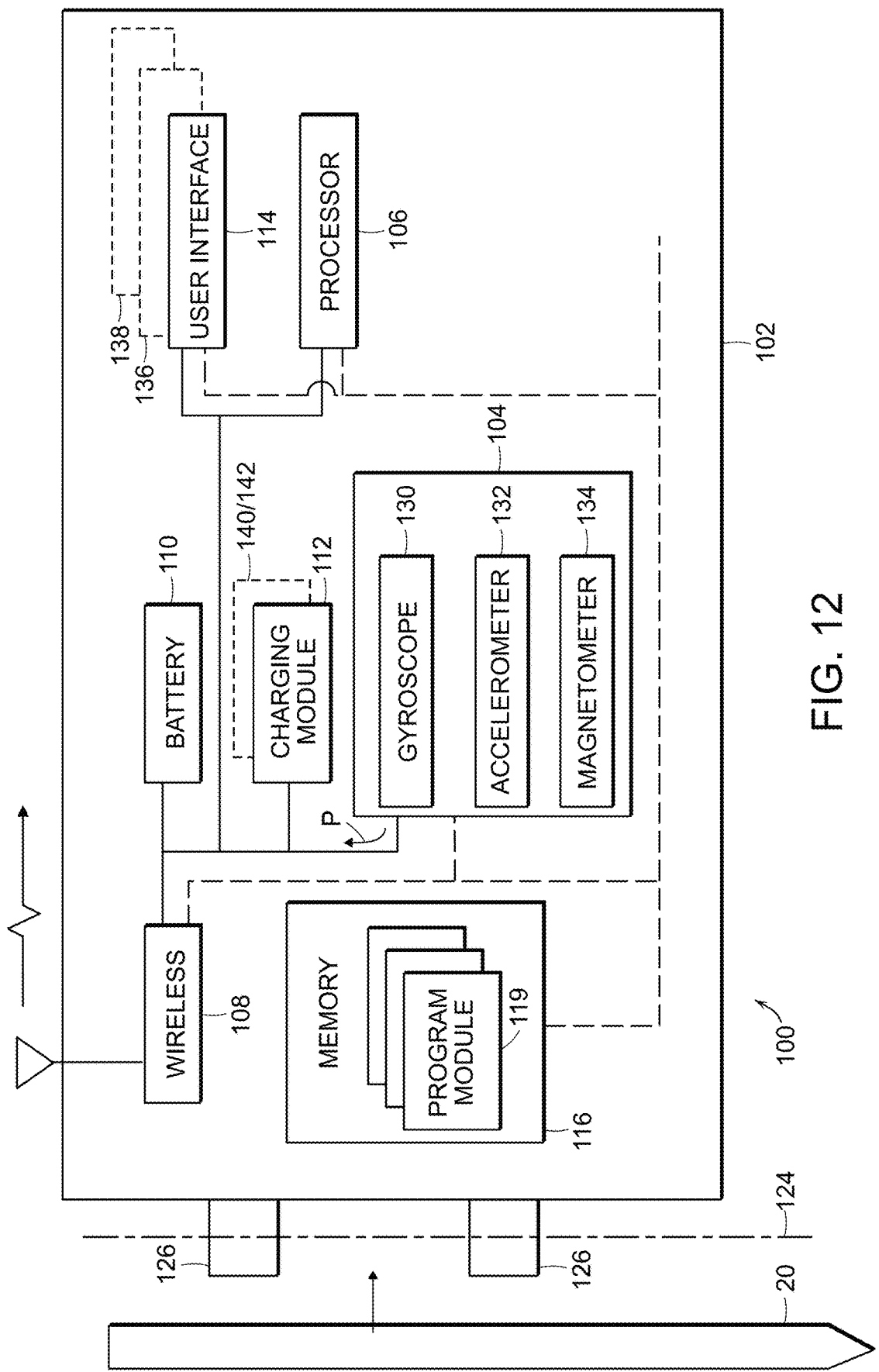
FIGS. 12-15 are a schematic and perspective views of the instrument tracker of FIG. 4, showing elements of the instrument tracker and the instrument being received within instruments arranged on the exterior of the instrument tracker case.
Figure 13:
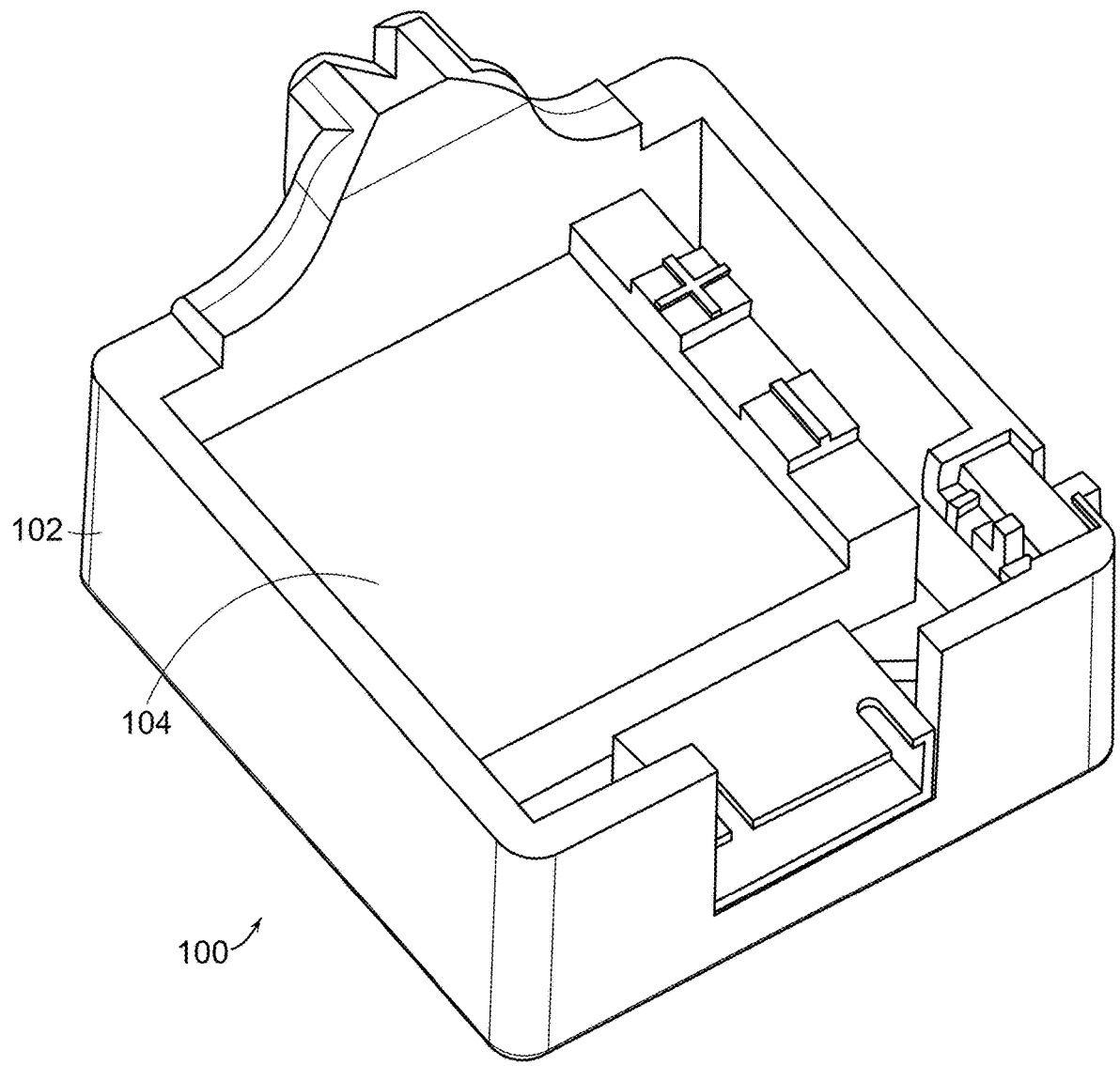
Figure 14:
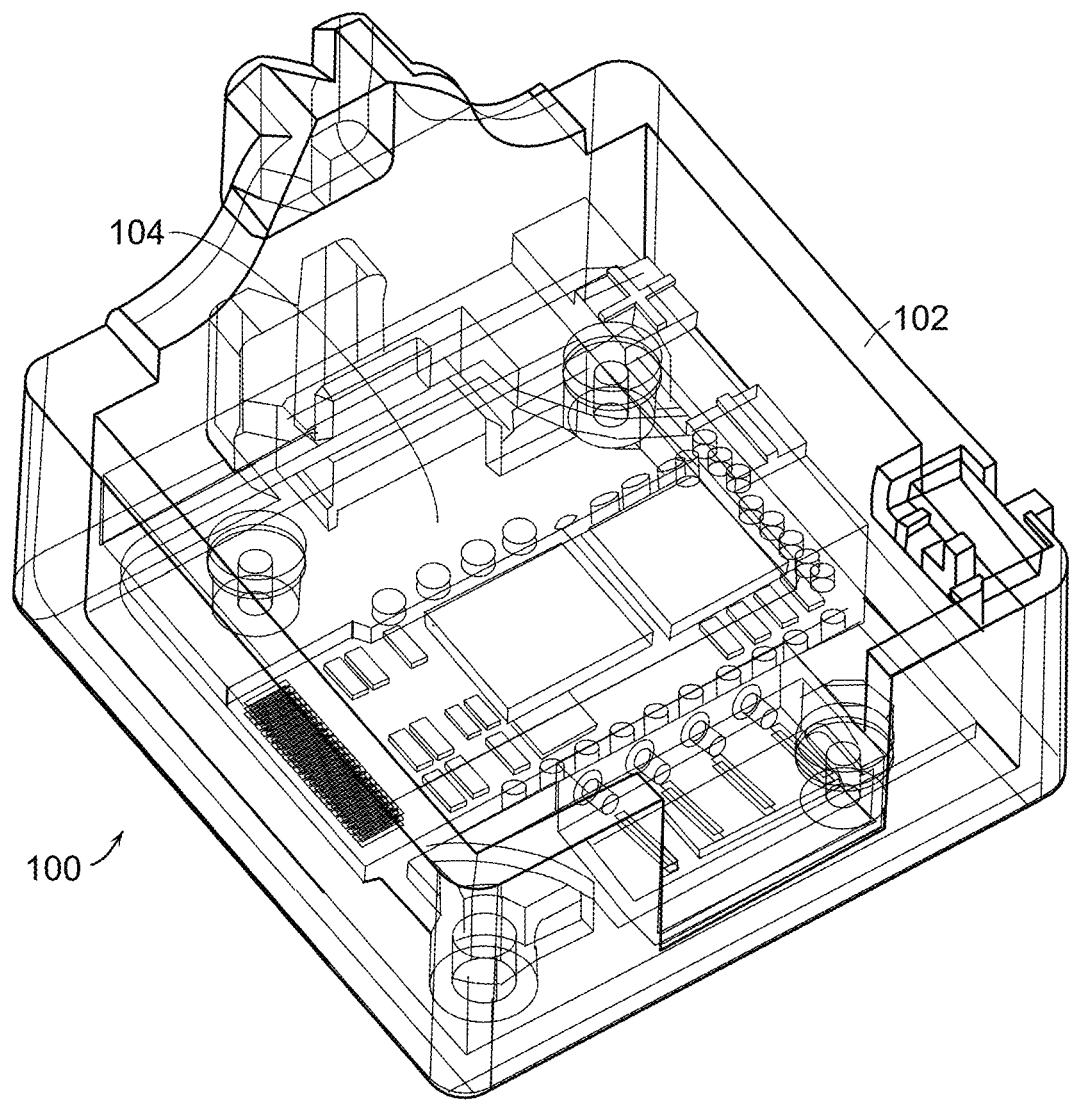

Display device 26 is in wireless communication with tracker controller 106 (shown in FIG. 12). Controller 34 (shown in FIG. 3) of display device 26 is in communication with memory 30 of display device 26, which has a non-transitory machine readable medium with instructions recorded on it that, when read by the display device controller 34, cause the display device controller to receive image data 24 of subject 10 (shown in FIG. 1) including region of interest 14 (shown in FIG. 1), define predetermined insertion path 42 (shown in FIG. 3) to region of interest 10 extending between entry point 44 (shown in FIG. 3) located on surface 12 (shown in FIG. 3) of subject 10 and region of interest 14, receive the at least one of position information 46 (shown in FIG. 4) and angular orientation information 48 (shown in FIG. 4) from instrument tracker 100 indicative of at least one of angular position and insertion depth of instrument 20 received within the plurality of instrument seats 126 (shown in FIG. 12) on case 102 (shown in FIG. 12) of instrument tracker 100, and display the at least one of the instrument angular position and insertion depth relative to predetermined insertion path 42 defined to the region of interest 14 located within subject 10. Although the data fusing and processing is shown in FIG. 11 as occurring on instrument tracker controller 106 (shown in FIG. 12), it is to be understood that the data fusing and processing can be done on the display unit controller 34 (shown in FIG. 3), such as in a smartphone or tablet app. As will be appreciated by those of skill in the view of the present disclosure, the data fusing can be done on both instrument tracker controller 106 and display unit controller 34, as suitable for an intended application.

Referring to FIGS. 12-15, instrument tracker 100 is shown. Instrument tracker 100 includes a case 102, an inertial measurement unit 104, and a controller 106. Instrument tracker 100 also includes a wireless communication module 108, a battery module 110, a charging module 112, and user interface module 114. A memory 116 having a non-transitory machine readable medium with a plurality of program modules 119 recorded on it is disposed in communication with controller 106.

Controller 106 has a processor and is disposed in communication with IMU 104 and memory 116. The instructions recorded in the plurality of program modules 119 on memory 116 cause controller 106 to perform certain operations to generate the at least one of position information 46 and angular orientation information 48 of instrument 20. More particularly, the instructions recorded in the plurality of program modules 119 cause controller 106 to receive position information P from IMU 104, determine at least one of position information 46 and angular orientation information 48 (e.g., insertion depth) of instrument 20, and transmit the at least one of position information 46 and angular orientation information 48 relative to subject 10 (shown in FIG. 1) and relation to region of interest 14 (shown in FIG. 1) located within subject 10 to display device 26 (shown in FIG. 2).

Display device 26 in turn determines the instrument position and instrument orientation, compares the instrument position and instrument orientation to a predetermined insertion path 42 (shown in FIG. 2) defined between an entry point 44 (shown in FIG. 2) located on the subject and the region of interest within the subject, and displays the comparison in an image 40 (shown in FIG. 3) to provide indication of position and orientation of instrument 20 relative the predetermined insertion path 42 (shown in FIG. 2)

Controller 106 is further operatively connected to wireless communication module 108 for wireless communication with display device 26 (shown in FIG. 2) to communicate thereto the at least one of position information 46 and angular orientation information 48 of instrument 20. Controller 106 is also operatively connected to user interface 114 for providing indication of the at least one of position information 46 and angular orientation information 48 of instrument 20 directly to user to user 50 (shown in FIG. 5).

User interface 114 is fixed relative to case 102 and is disposed in communication with controller 106, controller 106 thereby being operatively connected to user interface 114. In certain embodiments user interface 114 includes an auditory module 136, which is configured to provide auditory messages to user 50 (shown in FIG. 5). In accordance with certain embodiments user interface 114 includes a display module 138, which is configured to provide a visual indication directly to user 50, such as state of charge, etc. Battery module 110 is electrically connected to user interface 114 to provide a supply of electrical power to user interface 114.

Battery module 110 is electrically connected to wireless communication module 108, IMU 104, and controller 106 for providing a supply of electrical power wireless communication module 108, IMU 104, and controller 106. In certain embodiments battery module 114 is configured to provide about four (4) hours of power to instrument tracker 100. In accordance with certain embodiments battery module 114 have a charging cycle of about one (1) hour, thereby requiring a relatively short period of time for use. Charging can be accomplished using wireless charging module 112. Examples of suitable batteries include lithium batteries, e.g., DTP502535-PHR, capable of providing 400 mAh for about four hours of service between charging cycles.

Charging module 112 is electrically connected to battery module 110 for charging battery module 110. In certain embodiments charging module 112 can include a physical wire receptacle 140 for providing power to instrument tracker 100 and battery module 110. In accordance with certain embodiments charging module 112 can include a wireless charging module 142 for wireless charging battery module 110, such as with a coil and/or winding arrangement. As will be appreciated, wireless charging module 142 can simplify the arrangement of instrument tracker 100 while extending to time interval during which instrument tracker 100 can provide the at least one of position information 46 and angular orientation information 48 of instrument 20.

Wireless communication module 108 is configured and adapted for wireless communication of the at least one of position information 46 and angular orientation information 48 of instrument 20 to display device 26 (shown in FIG. 2). In this respect controller 106 is operatively connected to wireless communication module 108 and arranged to push the at least one of position information 46 and angular orientation information 48 of instrument 20 to display device via wireless communication module 108. The wireless communication can be via Bluetooth, WiFi, Zeebee, or any other wireless communication protocol, as suitable for an intended application.

Figure 15:
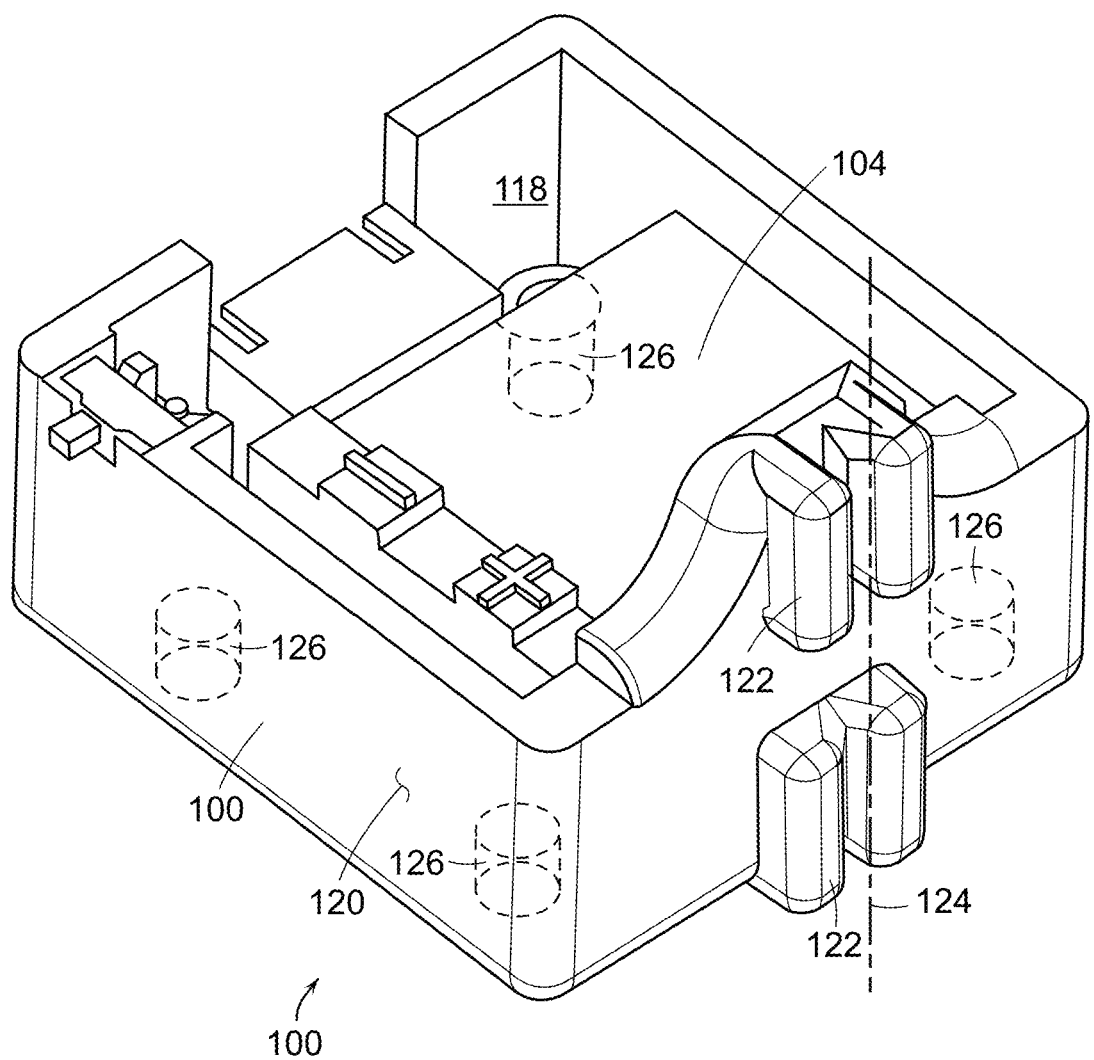

With reference to FIG. 15, case 102 is shown. Case 102 has interior 118, an exterior 120, and a plurality of instrument seats 122 arranged on exterior 120. Instrument seats 122 define an instrument channel 124 and are arranged to removably fix instrument 20 to instrument tracker 100. This allows instrument 20 to be received within the plurality of instrument seats 122, instrument 20 thereby being fixed relative to case 102. It is contemplated that case 102 can be formed using an additive manufacturing technique, such as by use of a Formlab® 3D printer, available from Formlabs Inc. of Somerville, Massachusettes. It is contemplated that case 102 can disposable or reusable with a sterilization cover bag.

As will be appreciated by the those of skill in the art in view of the present disclosure, supporting IMU 104 at a 90-degree angle suitable aligns the principle axis (or exes) of devices contained within IMU 104 to provide the at least one of position information 46 and angular orientation information 48 of instrument 20 relative to instrument tracker 100. As also shown in FIG. 12, case 102 can have four supports 126 arranged within interior 118 to support IMU 104. It is contemplated that supports 126 be arranged to support IMU 104 at an angle relative to instrument channel that is about 90-degrees.

Figure 16A:
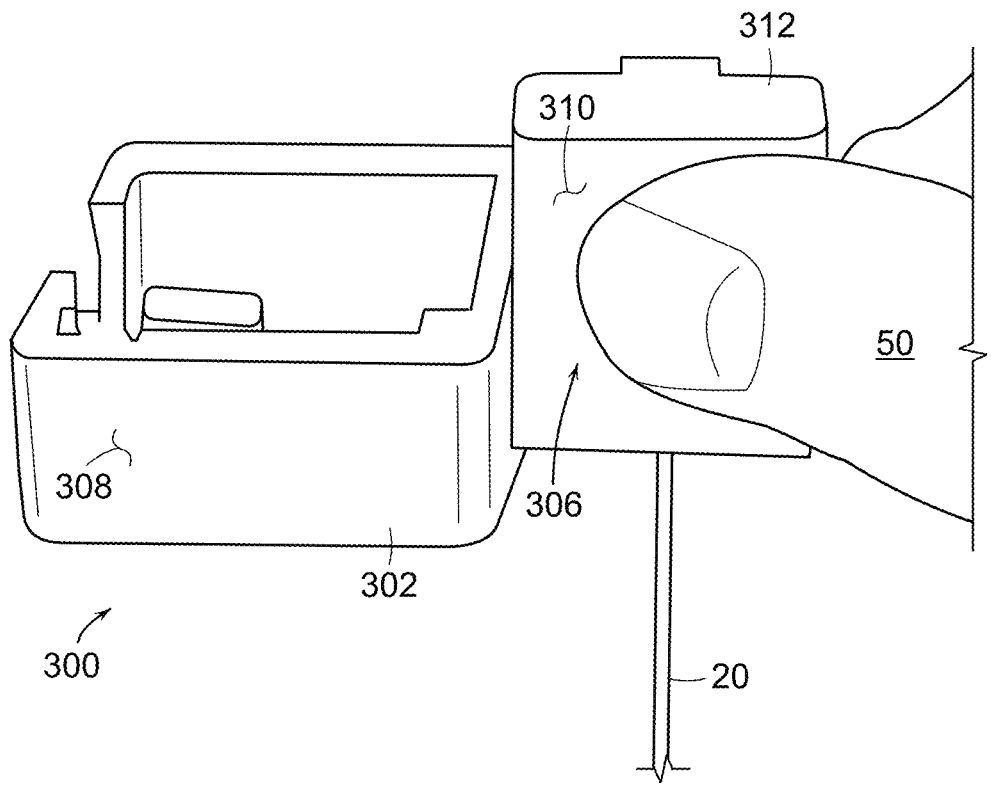
FIGS. 16A-16C are side elevation and perspective views of another embodiment of the instrument tracker of FIG. 2, showing a finger grip of the instrument tracker.
Figure 16B:
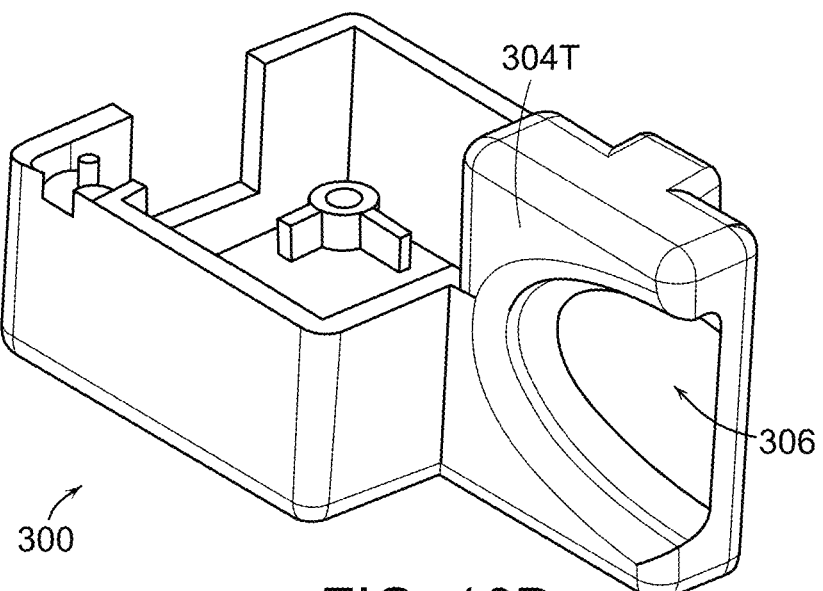
Figure 16C:
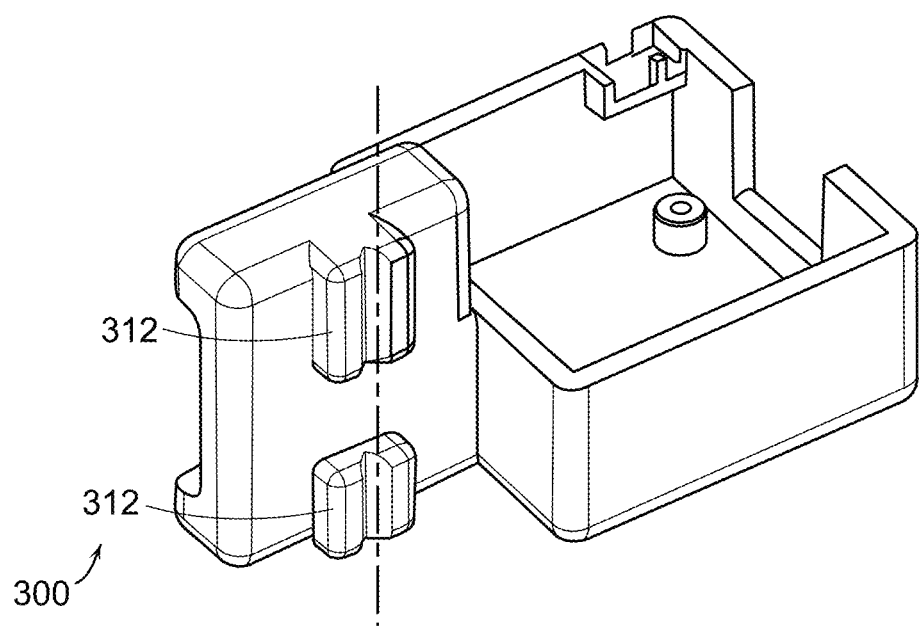

With reference to FIGS. 16A-16C, an instrument tracker 300 is shown according to an exemplary embodiment. Instrument tracker 300 is similar to instrument tracker 100 (shown in FIG. 3) and additionally includes a case 302. Case 302 includes a grip 304 with a finger seat 306. Finger seat 302 is disposed on an exterior 308 of case 302 and on a side 310 of grip 304 opposite the plurality of instrument seats 312. As will be appreciated by those of skill in the art in view of the present disclosure, the illustrated arrangement provides tactile engagement of user 50 suitable for manipulating instrument 20 with suitable control during insertion subject 10 (shown in FIG. 1) while providing the at least one of position information 46 and angular orientation information 48 of instrument 20 relative instrument tracker 300.

Figure 17:
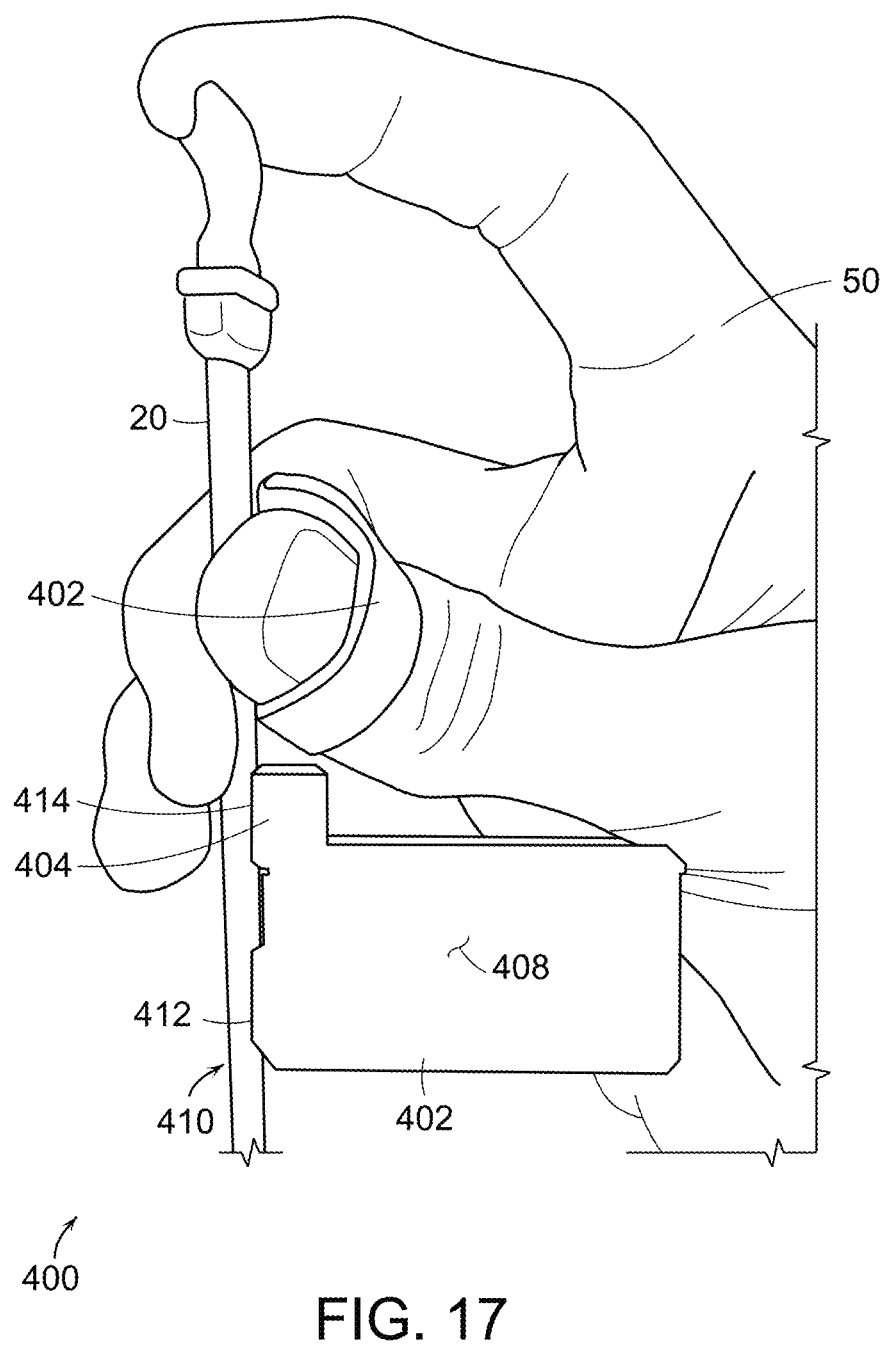
FIG. 17 is side elevation of yet another embodiment of instrument tracker of FIG. 2, showing a finger ring of the instrument tracker.

With reference to FIG. 17, an instrument tracker 400 is shown according to another exemplary embodiment. Instrument tracker 400 is similar to instrument tracker 100 (shown in FIG. 3) and additionally includes a case 402. Case 402 includes a grip 404 with a finger ring 406. Finger ring 406 is disposed on an exterior 408 of case 402. Finger ring 406 is arranged along instrument channel 410 such that a first 412 of the plurality of instrument seats is disposed on a side of a second 414 of the plurality of instrument seats opposite finger ring 406. As will be appreciated by those of skill in the art in view of the present disclosure, the illustrated arrangement also provides tactile engagement of user 50 suitable for manipulating instrument 20 with suitable control during insertion subject 10 (shown in FIG. 1) while providing the at least one of position information 46 and angular orientation information 48 of instrument 20 relative instrument tracker 400.

With continuing reference to FIGS. 12-15, IMU 104 is configured and adapted to provide the at least one of position information 46 and angular orientation information 48 of instrument 20 relative to instrument tracker 100 using one or more measurement device. In this respect IMU 104 includes at least one of a gyroscope 130, an accelerometer 132, and a magnetometer 134 for angular tracking required for instrument navigation in image-guided intervention therapies.

IMU 104 is an electronic device that measures and reports a body's specific force, angular rate, and sometimes the magnetic field surrounding the body, using a combination of accelerometers, gyroscopes, and/or magnetometers. IMU 104 operates by detecting linear acceleration using one or more accelerometers 132 and rotational rate using one or more gyroscopes 130. In certain embodiments IMU 104 employs the one or more magnetometer 134 to provide a heading reference. In certain embodiments IMU 104 includes one accelerometer, one gyroscope, and one magnetometer per axis for each of the three axes: pitch, roll and yaw.

In certain embodiments IMU 104 includes a vibrating structure gyroscopes manufactured with micro-electro-mechanical system (MEMS) technology. The MEMS-based IMU 104 is packaged like an integrated circuit and can provide either analog or digital outputs. In accordance with certain embodiments, a singular MEMS package includes gyroscopes 130 for more than one axis. It is contemplated IMU 103 can include a plurality of gyroscopes 130 and accelerometers 132 (or multiple-axis gyroscopes and accelerometers) to provide positional information and angular information indicative of six full degrees of freedom on instrument 20. Advantageously, IMU 104 implemented with MEMS device is relatively simple and inexpensive relative to rotating gyroscopes of having similar accuracy, and can be similar in arrangement to MEMS devices employed in smartphone, gaming device, and camera applications.

Magnetometer 134 is configured and adapted to measure magnetism—either magnetization of magnetic material like a ferromagnet, or the direction, strength, or the relative change of a magnetic field at a particular location. In certain embodiments magnetometer 134 has solid state devices cooperatively defining a miniature Hall-effect sensor, which detects the Earth's magnetic field along three perpendicular axes X, Y and Z. The Hall-effect sensor in turn produces a voltage which is proportional to the strength and polarity of the magnetic field along the axis each sensor is directed. The sensed voltage is converted to digital signal representing the magnetic field intensity. In certain embodiments magnetometer 134 can include one or more magneto-resistive device have resistance that changes based on changes in the magnetic field. It is contemplated that magnetometer 134 can be packaged in a small electronic chip, with or without another sensor device, e.g., accelerometer 132, for purposes of correcting the raw magnetic measurements using tilt or gyroscopic information from co-packaged sensor device. In addition to providing rotational information, magnetometer 134 can provide information for detecting the relative orientation of instrument tracker 100 relative to the Earth's magnetic north.

In the illustrated exemplary embodiment IMU 104 includes each of gyroscope 130, accelerometer 132, and magnetometer 134. In certain embodiments IMU 104 can include a plurality of gyroscopes, a plurality of accelerometers, and a plurality of magnetometers.

In an exemplary embodiment instrument tracker 100 has a needle guide, a solid case, and electronics of one or more IMUs and/or magnetometers, batteries, one or more controllers, wire and wireless charger modules, wire and wireless communication modules, and audio and visual indicator electronics. The IMU and magnetometer measure the orientation and positional information of the needle guide by fusing the acquired data. The controller provides kinematic calculation, a manages communication between internal audio and visual indicators and external computer, tablet, smartphone devices that display navigation information. The battery provides power of the tracker. A charger module charges the battery of the tracker in the form of wire and/or wireless charging. A communication module connects an external device, including a computer, a tablet, and/or a smartphone device using wire or wireless communication module including but not limited to Bluetooth, WIFI, Zeebee or other wireless communication protocol. The needle guide is configured to allow an instrument to pass through for use in the guided interventional medical procedure.

Figure 18A:
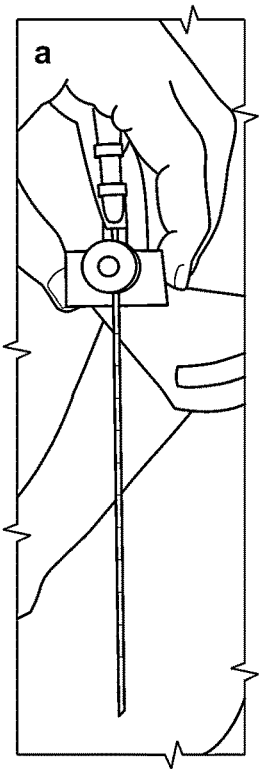
FIGS. 18A-18C are images of an experimental arrangement employing the instrument tracker of FIG. 2, showing the instrument tracker being used to guide instruments to regions on interest within the anatomy of a subject, FIG. 18A showing the instrument tracker as a clip added on different medical devices and/or needle instruments, FIG. 18B showing an instrument removably fixed to the instrument tracker inserted in a subject, and FIG. 18C showing the instrument tracker IMU with MEMS-based gyroscope, gravity sensor, and Bluetooth communication module, battery with 4 hours of charge.
Figure 18B:
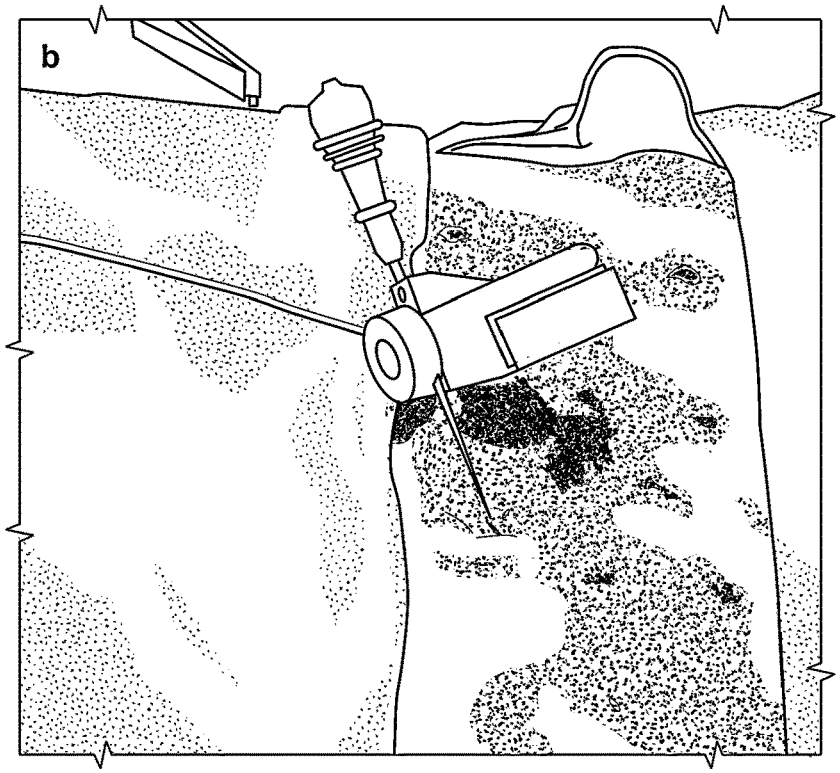
Figure 18C:
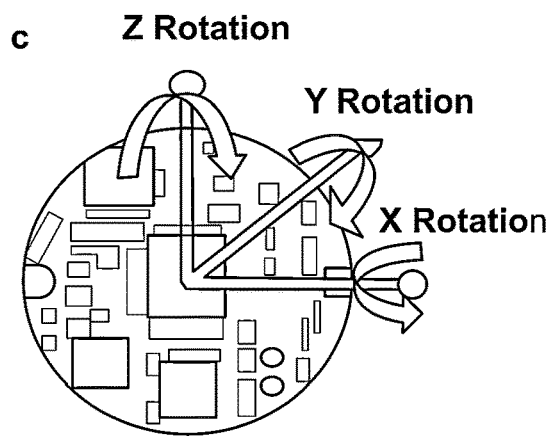

With reference to FIGS. 18A-18C, instrument tracker 100 can provide a compact wireless device that can be clipped onto any medical device/needle instrument. Further, instrument tracker 100 can provide 6 degrees-of-freedom (DOF) sensing (3DOF from the gyroscope, 3DOF from the accelerometer, and 3DOF from the magnetometer). Moreover, instrument tracker 100 can be configured to wirelessly stream data via Bluetooth and has embedded rechargeable battery.

In an aspect instrument tracker 100 can employ sensor fusion. More particularly IMU 104, which can have one or more of an accelerometer, a gyroscope, and a magnetometer, and the measured gravity vector together with data fusion and signal processing methods to enhance needle tracking accuracy. Combining a magnetometer with a gravity sensor can help correct for gyroscope drift. Employing sensor models and a sensor fusion algorithm an accurate estimate of orientation given the inertial guidance input can be provided.

In another aspect no pre-calibration is required for in-axial-plane needle insertions. Instead, during instrument tracking the needle angles (e.g., X and Y axis rotations) are dynamically adjusted with the gravity vector to ensure its accuracy by eliminating accumulative errors caused by gyroscope drifts. In-axial-plane needle instrument insertion is the most common approach in CT-guided procedures.

Figure 19A:
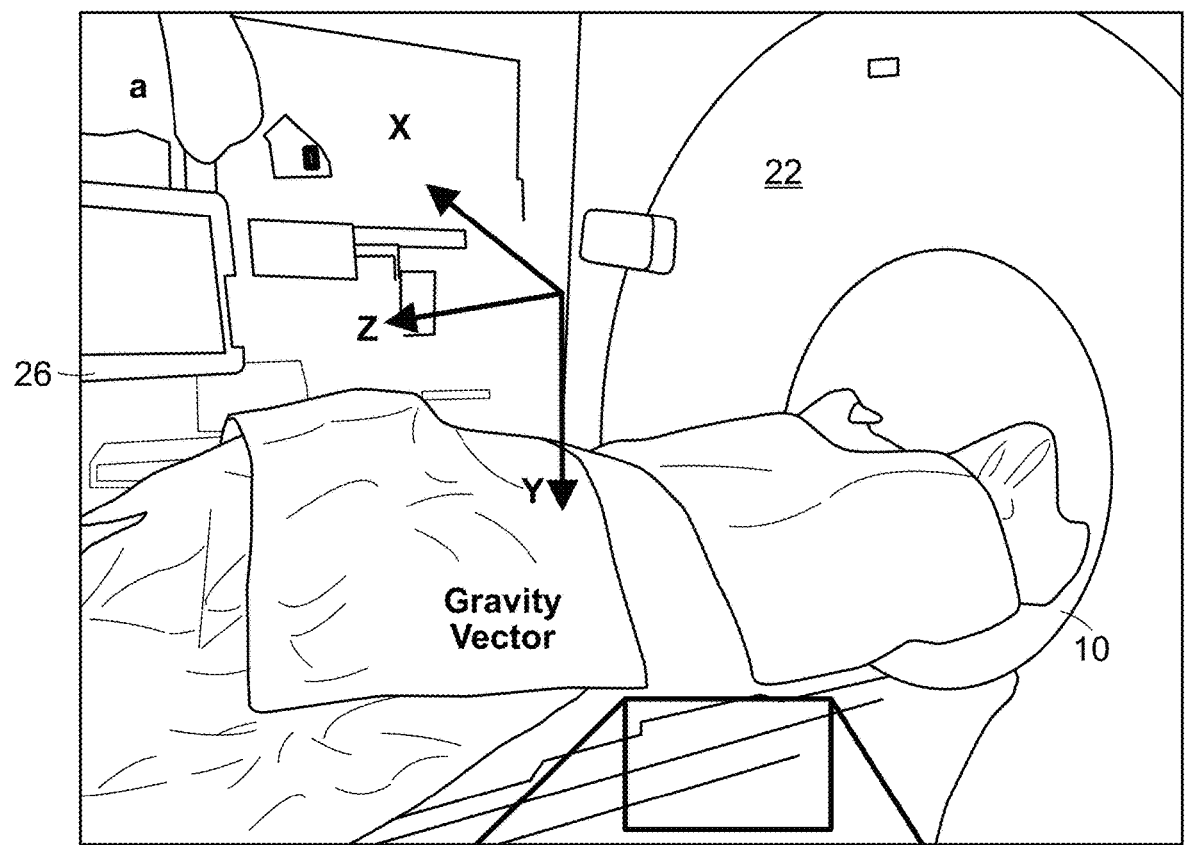
FIGS. 19A and 19B are perspective views of instrument tracking system of FIG. 11, showing the instrument tracker calibrated using the edges of an imaging device subject table for orientation alignments.
Figure 19B:
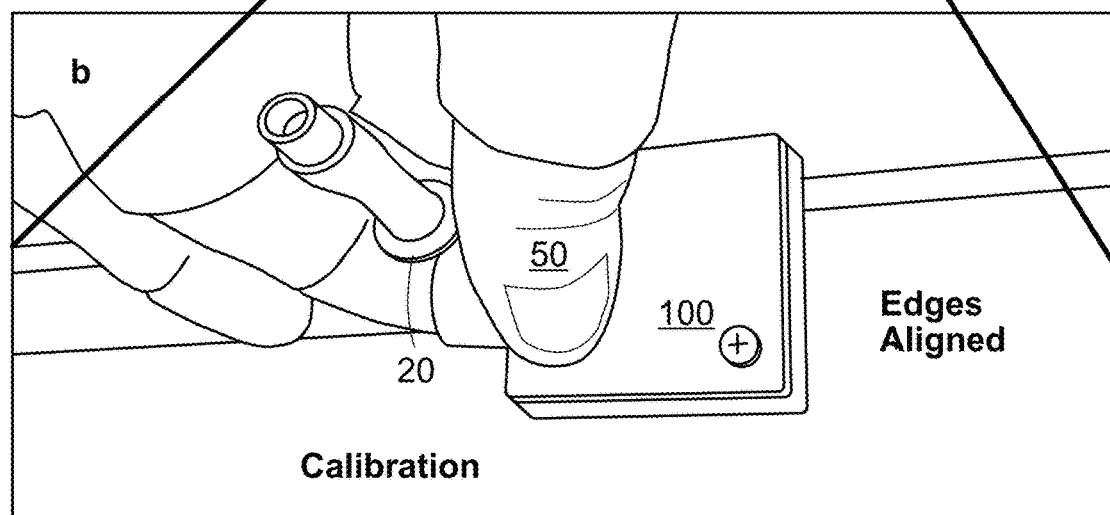

With reference to FIGS. 19A-19B, calibration of instrument tracker 100 is shown. In a further aspect one-touch calibration can be used for off-axial-plane needle insertion. In this respect, for tumor targets at different locations requiring off-plane targeting, a calibration procedure of the instrument tracker can be done in a fast and simple one-touch step. Calibration can be accomplished by placing instrument tracker 100 at any two perpendicular edges of the CT table that aligns the tracker to the X and Z-axes of the CT table, as shown in FIG. 19B. The calibration can be takes approximately a few seconds to generate the calibration matrices and can be performed prior to instrument insertion.

Figure 20:
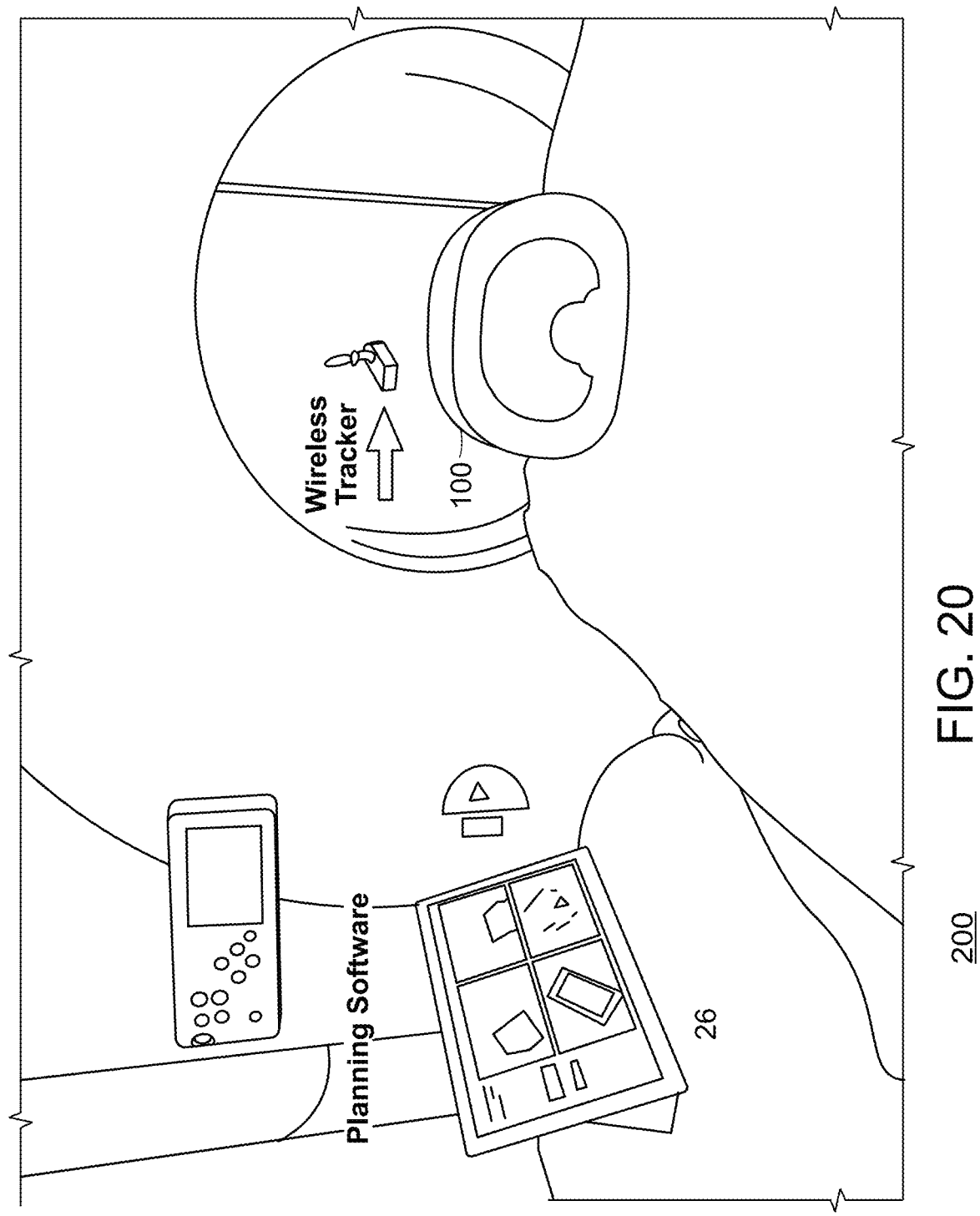
FIG. 20 is a perspective view of the instrument tracking system of FIG. 11, showing the instrument tracker and display device being used in conjunction with an imaging device during imaging an anthropomorphic abdominal model.

With reference to FIG. 20, instrument tracking system 200 is shown. It is contemplated that display device 26 and instrument tracker 100 feature an optimized clinical workflow for CT-guided needle ablative procedures, which has been tested for targeting accuracy of ablations in tumors using an anthropomorphic abdominal phantom and using swine models. Program modules on instrument tracker 100 and display device 26 can be configured for computer Windows OS, and a lightweight version of the software application is also available on smartphones and tablets (FIG. 3). In certain embodiments the program modules include one or more of three-dimensional volumetric rendering, segmentation, treatment planning, and visualization of regions of interest 14 (e.g., tumor targets) and obstacles 18 (e.g., adjacent structure). User 50, such as a physician, uses the application interface to view and edit segmentation results; contribute to trajectory planning by indicating possible needle insertion points; review and, if necessary, change the treatment plan; and deliver ablations.

Display device 26 can include a computer device, a tracking device, an imaging device, a template (or needle guide assembly), one or more surgical device or surgical device assemblies, a dynamic reference device, or other components. Further, display device 26 can be communicative with one or more servers, personal computers, portable (e.g., laptop) computers, mobile computers, tablet computers, cell phones, smart phones, PDAs, or other computer devices. Computer device may send, receive, store, or manipulate data necessary to perform any of the processes, calculations, image formatting, image display, or other processing operations described herein. The computer devices may also perform any processes, calculations, or processing operations necessary for the function of the devices, instruments, or other system components described herein. The computer device may include one or more processor(s), one or more storage device(s), a power source, a control application comprising computer program instructions, one or more inputs/outputs, at least one display device, one or more user input devices, or other components.

Processor(s), such as those within the controllers, may include one or more physical processors that are programmed by computer program instructions that enable various features and functionality described herein. For example, processor(s) may be programmed by control application (described below) and/or other instructions.

Storage device may comprise random access memory (RAM), read only memory (ROM), and/or other memory. The storage device may store the computer program instructions to be executed by processor(s) as well as data that may be manipulated by processor(s). Storage device may also comprise floppy disks, hard disks, optical disks, tapes, or other storage media for storing computer-executable instructions and/or data.

The actual display of display device 26 can include a computer monitor or other visual display device such as, for example, an LCD display, a plasma screen display, a cathode ray tube display, or other display device. The user interface of display device 26 can include a mouse, a stylus, a keyboard, a touchscreen interface (which may be associated or integrated with display device), a voice-activated input device (e.g., including a microphone and/or associated voice processing software), or other device that enables a user (e.g., a physician performing a procedure, an assistant thereto, or other user) to provide input to computer device and/or other components of system. One or more input devices may be utilized. In one implementation, display device and input device may together be configured as a mobile computing platform such as a tablet computer that is connected wirelessly to computer. Other configurations may be implemented. Inputs/outputs enable various system components such as tracking device, imaging device, template (or needle guide assembly), one or more surgical device or surgical device assemblies, dynamic reference device, or other components to communicate with computer device (e.g., in a wired or wireless manner) as known and understood by those having skill in the art.

Display device 26 can be connected to other computer devices and/or other system components via a network, which may include any one or more of, for instance, the Internet, an intranet, a PAN (Personal Area Network), a LAN (Local Area Network), a WAN (Wide Area Network), a SAN (Storage Area Network), a MAN (Metropolitan Area Network), a wireless network, a cellular communications network, a Public Switched Telephone Network, and/or other network.

Display device 26 can be operatively connected (e.g., via the aforementioned network) to one or more databases. A database may be, include, or interface to, for example, an Oracle™ relational database sold commercially by Oracle Corporation. Other databases, such as Informix™, DB2 (Database 2) or other data storage, including file-based, or query formats, platforms, or resources such as OLAP (On Line Analytical Processing), SQL (Structured Query Language), a SAN (storage area network), Microsoft Access™ or others may also be used, incorporated, or accessed. The database may comprise one or more such databases that reside in one or more physical devices and in one or more physical locations. The database may store a plurality of types of data and/or files and associated data or file descriptions, administrative information, or any other data, as described herein.

Imaging device 22 can include an x-ray imaging device, computerized tomography imaging device, a positron emission tomography imaging device, a magnetic resonance imaging device, a fluoroscopy imaging device, an ultrasound imaging device, an isocentric fluoroscopic imaging device, a rotational fluoroscopic reconstruction imaging device, a multi-slice computerized tomography imaging device, an intravascular ultrasound imaging device, an optical coherence tomography (OCT) device, an optical imaging device, a single photon emission computed tomography imaging device, a magnetic particle imaging device, or any other suitable imaging/scanning imaging device. In certain embodiments, imaging device 22 may include one or more instrument tracker 100 so that the location and orientation of the imaging device 22 may be tracked by the one or more instrument tracker 100. For example, an ultrasound imaging device may include a position-indicating element enabling its scan plane to be known. Similarly, a fluoroscopic imaging device may include a tracking target. In certain embodiments a template (or needle guide assembly) assembly can be employed using template (also referred to as a targeting template or needle guide) and a position-indicating element or template tracker, which may be attached (permanently or removably) to the template or to a frame that surrounds (or encompasses) all or a portion of the template.

Template tracker may comprise a mechanical template that can be tracked by the tracker. The template (or needle guide assembly) may further comprise a support mechanism or structure used to support and/or position the template assembly vis-à-vis a target (e.g., a patient's anatomy). The support mechanism may comprise dials or other controls to adjust and fine tune the position of the template. Examples of a support mechanism may include a Biojet (D&K Technologies GmbH, Barum Germany) or the Multi-purpose Workstation LP (Civco Inc., Coralville Iowa) that may include motors and/or encoders. In certain embodiments, the template assembly may be supported and/or moved into position in an automated manner using a robotic mechanism attached to the support mechanism.

In accordance with certain embodiment, instrument tracking system 200 may include one or more surgical devices or device assemblies, the position and orientation of which may be tracked by tracking device. Examples of surgical devices may include therapeutic devices such as needles, ablation needles, radiofrequency ablation needles, lasers and laser delivery systems, blades, cryoablation needles, microwave ablation needles, HIFU delivery systems, and radiation delivery devices, or other therapeutic devices. Monitoring probes for measuring temperature or dose, etc. may also be used along with probes that perform a protective function such as cooling an area that is adjacent to a region that is being ablated using heat, etc. In some implementations, needles may further serve as elements that also restrain the anatomy from motion.

In further embodiments a dynamic reference device can be employed. For example, instrument tracking system 200 can include a dynamic reference device capable of tracking a patient's anatomy. Examples of dynamic reference device may include, but are not limited to, a tracked Foley catheter, a skin patch, etc.

The controller can employ a control application, such as a host control application. The control application can include a computer software application that includes instructions that program processor(s) (and therefore computer device) to perform various processing operations. For example, the control application may cause computer device to send, receive, and/or manipulate data regarding the anatomy of a patient, one or more objects, or other data. This data may be stored in memory device, or in another data storage location (e.g., the one or more databases described above). In certain embodiments the computer device may receive live data (in real-time) or stored data. The computer device may send, receive, and/or manipulate data regarding the location, position, orientation, or coordinate(s) of a position indicating element (e.g., sensor coils or other position indicating elements), or one or more other elements, received by tracking device. This data may also be stored in memory device or in another data storage location (e.g., the one or more databases described above).

Control application may further cause computer device to produce, format, reformat, or otherwise manipulate one or more images, position/orientation/location data, or other data. Images may be displayed on display device. In some implementations, one or more live images may be displayed. Display device may further display (or otherwise convey) audio data in addition to, or instead of, visual data. Such an audio display may produce tones or other indicators regarding the system.

Control application may additionally cause computer device to generate and display images of the anatomy of a patient along with the position or orientation of an instrument, fiducials, or both (or other information) superimposed thereon in real-time such that motion of the tracked instrument within the anatomy of the patient is indicated on the superimposed images for use in an image-guided procedure.

In certain embodiments, indicators (e.g., markings, lines, circles, spheres, letters, numbers or other indicators) may be produced on an image of the anatomy of a patient. These indicators may mark or identify features such as the boundaries of another image stored in memory device.

In further embodiments the control application may facilitate mapping of a target lesion (e.g., a cancerous region) or other portion of a patient's anatomy, or other operations related to a map of the target lesion or portion of the patient's anatomy. For example, control application may generate and display (e.g., on display device) the position of a tracker relative to a location in a target lesion, a projected path (of the target paths of the tracker) including a path a needle or other instrument inserted into a hole (or a needle guide or a channel) of the tracking device will follow if the needle or instrument is extended past a distal end portion of the tracker. Control application may additionally generate and display (e.g., on display device) a point at which a needle or other instrument placed in a hole of the tracker will intersect a target lesion if the projected path of the needle or instrument intersects the determined path of the target lesion, as well as an indicator of the closest approach from a needle or other instrument passing through a hole in the tracker to the target lesion if the projected path of the needle or instrument does not intersect tissue not intended to be treated or biopsied. Additional displays may be presented. The foregoing system architecture is exemplary only, and should not be viewed as limiting. The invention described herein may work with various system configurations. Accordingly, more or less of the aforementioned system components may be used and/or combined in various implementations.

Figure 21A:
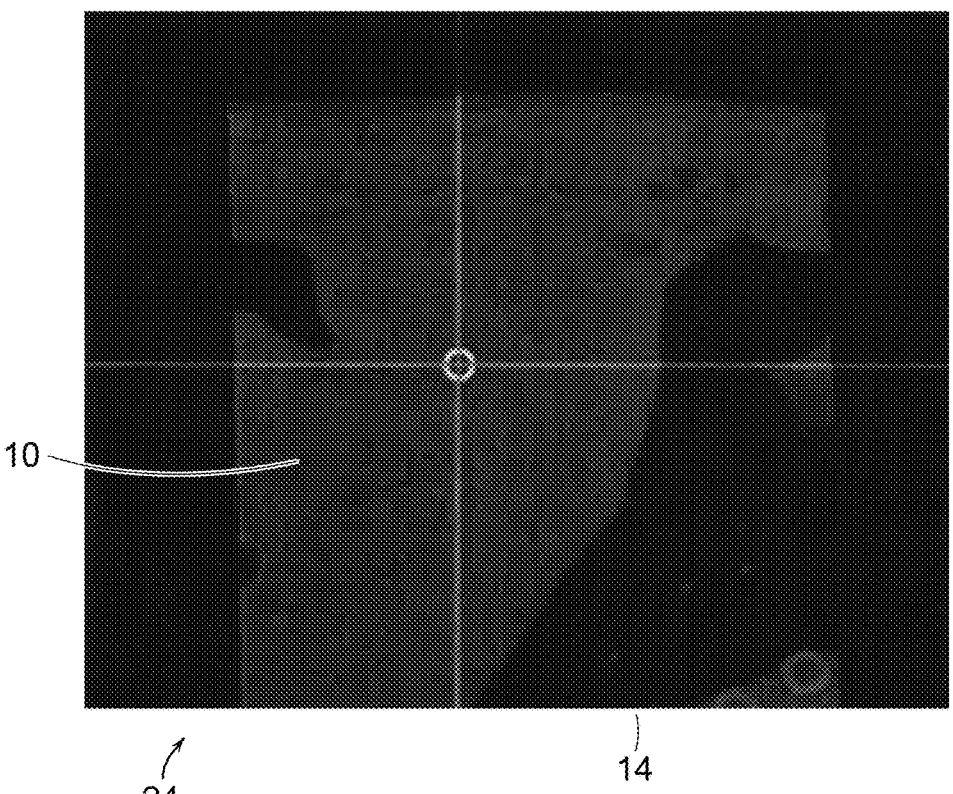
FIGS. 21A-21D are images generated by the display device of the instrument tracking system of FIG. 11, showing images of multiple planes reconstructed from CT images and three-dimensional views of the subject prior to and after instrument insertion into a region of interest.
Figure 21B:
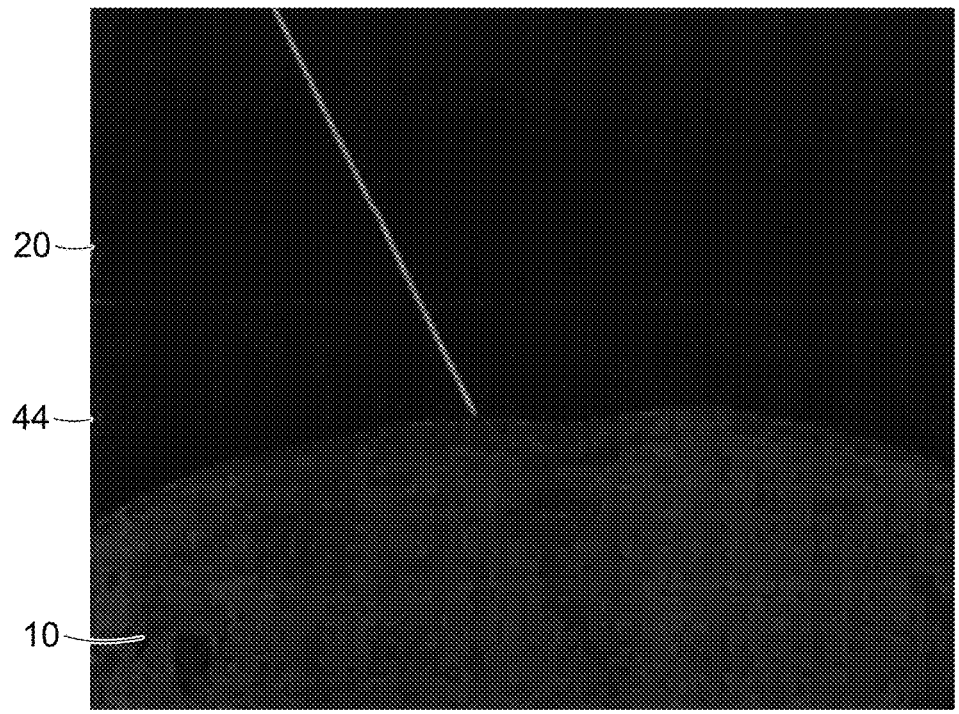
Figure 21C:
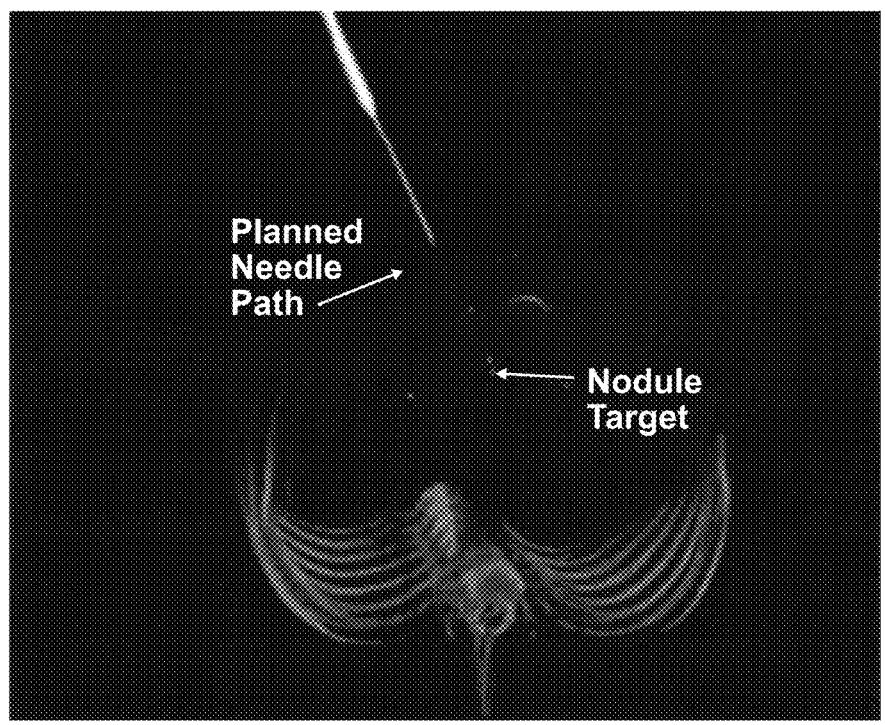
Figure 21D:
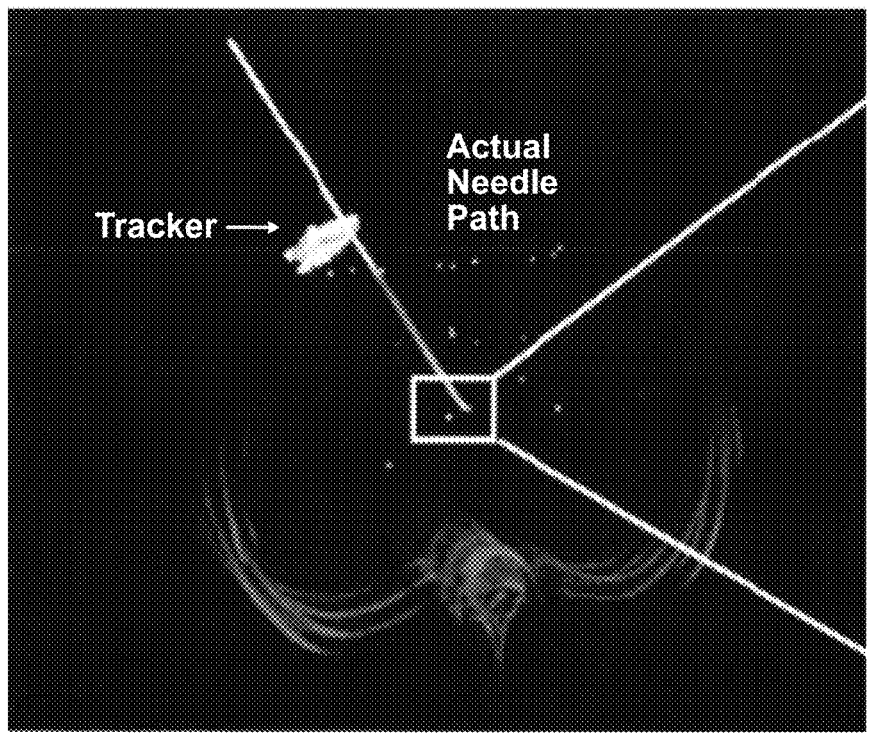

With reference to FIGS. 21A-21D, a method 500 of tracking position of an instrument, e.g., instrument 20 (shown in FIG. 3), is shown. Method 500 includes imaging a subject including a region of interest, as shown in FIG. 21A. An insertion path is defined between an entry point, e.g., entry point 44 (show in FIG. 3) an instrument includes fixing an instrument tracker, e.g., instrument tracker 100 (shown in FIG. 3), to the instrument, as shown in FIG. 21B. The instrument is registered with the entry point, as shown in FIG. 21C, and the instrument inserted into the subject along the insertion path, as shown in FIG. 21D.

As the instrument is inserted into the subject positional information is received from an IMU, e.g., IMU 104 (shown in FIG. 4), of the instrument tracker. The positional information is used to determine at least one of angular orientation and insertion depth of the instrument using the information received from the IMU.

The at least one of the angular orientation and insertion depth of the instrument is transmitted to a display device disposed in communication with the instrument tracker, the at least one of angular orientation and insertion depth of the instrument compared to a predetermined instrument insertion path defined between an entry point, located on the subject, and the region of interest within the subject. Based on the difference between the at least one of angular orientation and insertion depth of the instrument to the instrument path displayed on the display device user 50 (shown in FIG. 5) makes adjustments to the position of the instrument.

In certain embodiments program modules 38 (shown in FIG. 3) is configured to receive DICOM images from imaging device 22 (shown in FIG. 2), e.g., through the CT scanner host workstation. A four-quadrant display can be generated containing 2D and 3D rendered volumetric CT images of the tumor, vasculature, and other peripheral structures, as shown in FIG. 21A. Responsive to a prompt the user can then select an entry point on the surface of the subject and a region of interest within the subject, and an insertion path thereafter be defined. It is contemplated that insertion paths to various region of interest be defined (or optimized) to avoid obstacles, such as critical structures during insertion. The user can then select an insertion path and the display device assists the user with carrying out the treatment plan by providing visual targeting assistance and image overlay.

In certain embodiments ablation locations and needle trajectories are determined by solving an optimization problem for a given tumor volume and adhering to the constraints set, such as rules requiring (a) minimizing the number of ablations to reduce treatment time and probability of complication; (b) limiting the number of instrument insertions, e.g., by preferentially selecting reinserts of an instrument through previous insertion entry points and/or performing multiple ablations along the same linear trajectory; (c) incorporating instrument trajectory constraints such as anatomical physical/spatial restrictions associated with irregularly shaped regions of interest, as can be the case with tumor targets. In further embodiments instrument tracking system 200 can uses segmented image data from a specific subject (e.g., by-name patient) so treatment planning is specific to the individual's unique anatomy.

Figures 22A, 22B, 22C:
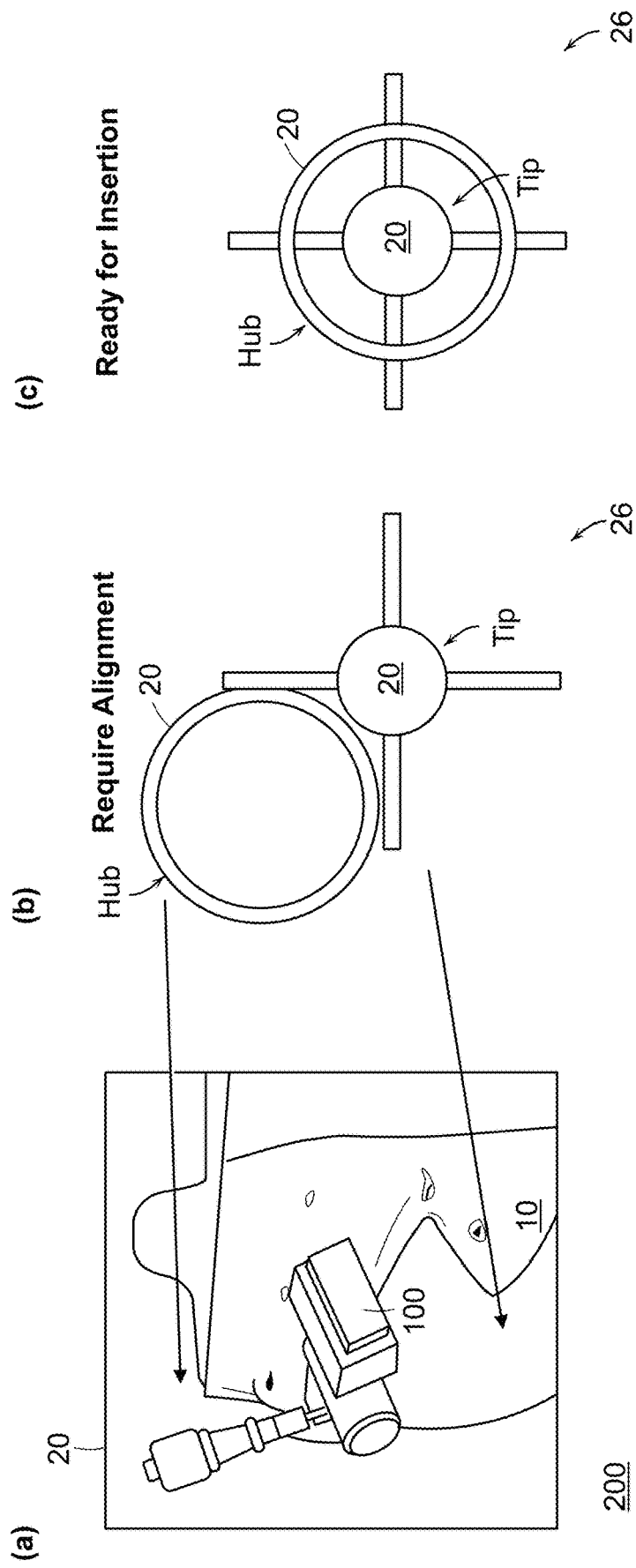
FIGS. 22A-22C are an image and registration indicators provided by the display device of the instrument tracking system of FIG. 11, showing the registration of the instrument with an entry point located on the surface of the subject relative to a tip and hub of a needle instrument.

With reference to FIGS. 22A-22C, intra-procedural visual guidance for assisting in instrument positioning is shown. As shown in FIGS. 22B and 22C, a visual guidance bullseye view for off-plane needle navigation provides pointing knowledge of an instrument 20 relative to predetermined insertion path 42 (shown in FIG. 3). In the first step, a tip of instrument 20 needle is placed at entry point 44 (shown in FIG. 3) as identified in a reconstructed image, e.g., image 40 (shown in FIG. 3). First a circle, e.g., a blue circle, is generated in image 40 on display device 26 to represent the tip of instrument 20 and a crosshair generated in image 40 to represent the region of interest 14 (shown in FIG. 1) in subject 10 (shown in FIG. 1). A shaft of instrument 20 is then generated, e.g., as a red circle, and is aligned towards the correct insertion angle while maintaining the tip of instrument 20 at entry point 44. User 50 then drives the shaft circle into registration with tip circle while retaining the tip of instrument 20 at entry point 44. Optionally, angular error can be displayed within the shaft circle. When the shaft circle is centered on the crosshairs the angle of instrument 20 is aligned to the angle of predetermined insertion path 42, and instrument 20 inserted to the desired depth using the above described position information provided by instrument tracker 100 and instrument tracking system 200.

Figure 23A:
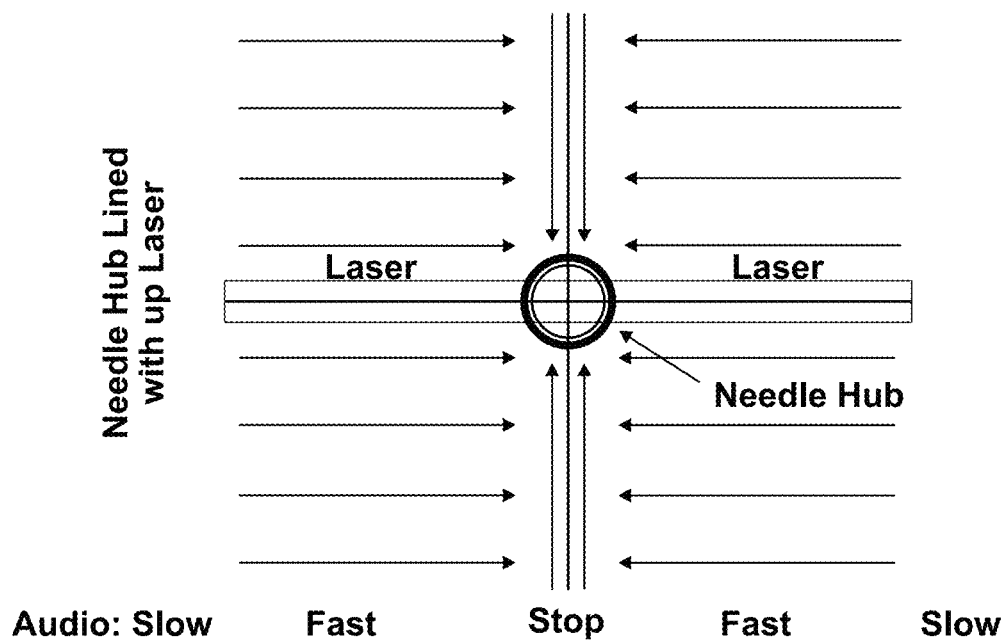
FIGS. 23A and 23B are a display scheme and images of instrument tracking using the instrument tracking system of FIG. 11, showing an auditory display for angular navigation in CT in-axial-plane targeting.
Figure 23B:
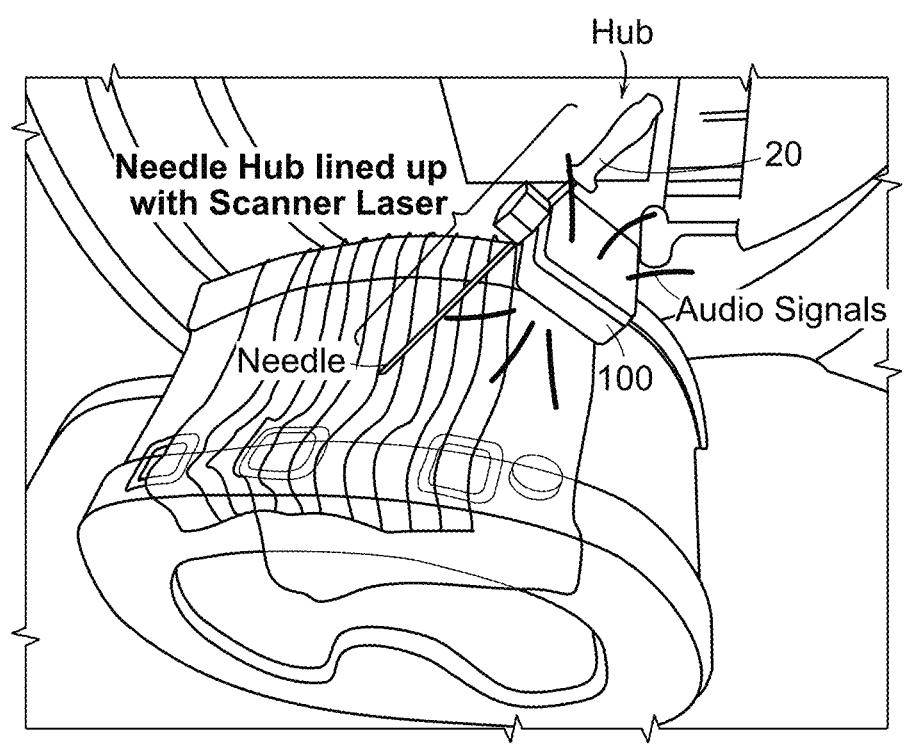

With reference to FIGS. 23A and 23B, insertion of instrument 20 is shown with auditory guidance. As shown in FIG. 23A, as user (e.g., a physician) moves instrument 20 in-axial-plane with the CT axial image by aligning the instrument tip and the instrument hub of a needle instrument with the laser plane at the CT scanner gantry instrument tracker generates audio signals. The audio signals denote the in-axial-plane angular position of needle instrument 20. Changes in absolute angle are linearly mapped to speed between pulses, slow at the left and right edges, progressing faster towards the center of the planned angle, and finally stop at a small angle, such as ±1 degree within the planned angle, denoting the correct angle for insertion. The auditory display shown in FIG. 23A can be generated in instrument tracker 100, in display device 26 (shown in FIG. 3), or in another external device such as a computer, tablet or smartphone devices via a wireless communication protocol.

The auditory display can include but not limiting to the form of (1) intermittent sound beeps with different time intervals, (2) sound with different frequency pitches, and (3) audio read-outs of the angle degrees, to represent the spatial alignment between the needle and the tumor target. The auditory display can also be replaced or shown simultaneously with the visual display in the tracker or through an external computer, tablet or smartphone devices via a wireless communication protocol.

Figure 24A:
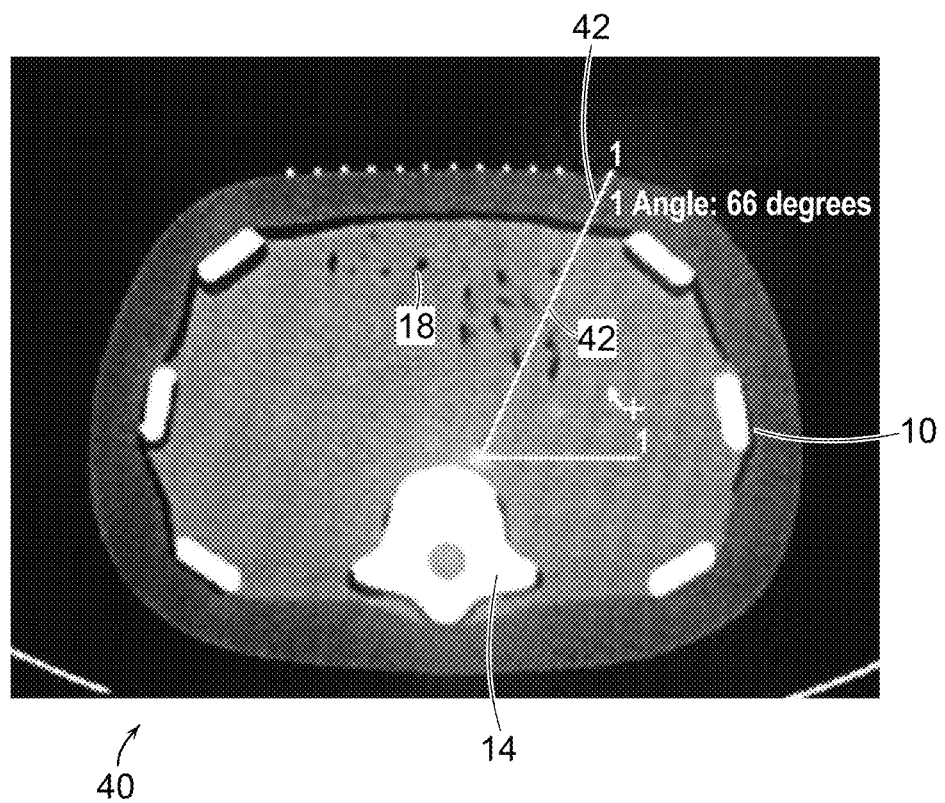
FIGS. 24A and 24B are proof of concept images, showing a planned instrument insertion path angle and an actual instrument insertion angle using the instrument tracker, instrument tracking system, and method tracking position of an instrument according to embodiments described herein.
Figure 24B:
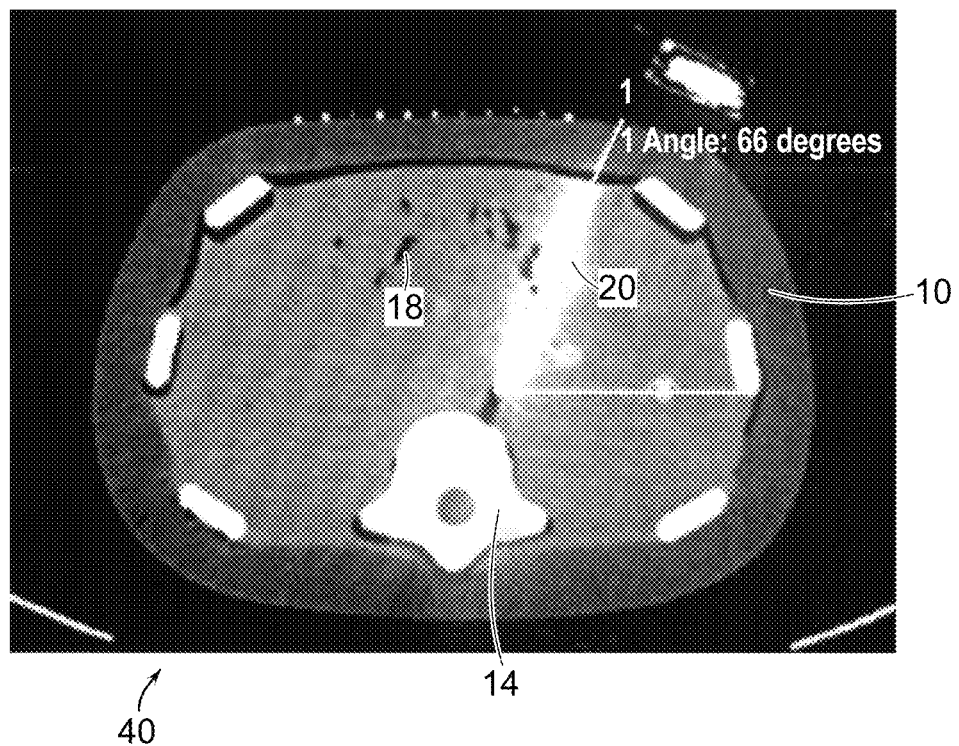

With reference to FIGS. 24A-24B, proof of concept is shown. As shown in FIG. 24A, an entry point 44 and predetermined insertion path 42 are defined in subject 10 and displayed in image 40. Predetermined insertion path 42 has a planned angle of about 66 degrees. FIG. 24B shows instrument 20 inserted in subject 10 along predetermined insertion path 42 and into region of interest 14. Notably, image 40 shows instrument 20 with an angle of about 66 degrees. This demonstrates that instrument trackers, instrument tracking systems, and method of tracking instruments described herein can for accurately position instruments in regions of interest within subjects, particularly in intervention procedures targeting deep-seated tumors.

Figures 25A, 25B:
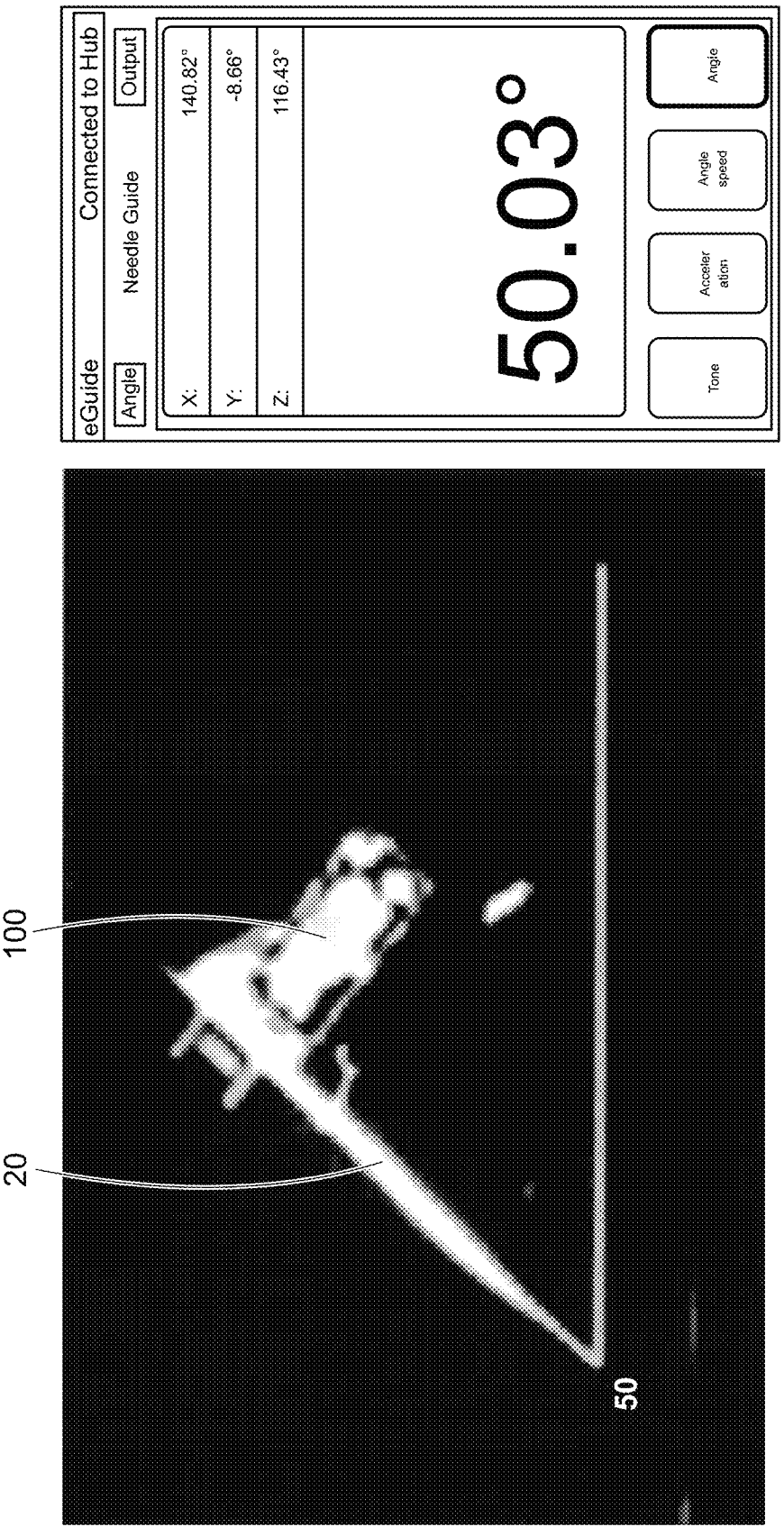
FIGS. 25A and 25B are images generated on the display device of the instrument tracking system of FIG. 11, showing a smartphone device for angular navigation in CT in-axial plane targeting, FIG. 25A showing a CT image of the needle and instrument tracker unit in CT in-axial-plane, and FIG. 25B showing a display of the angle on a smartphone display device application.

With reference to FIGS. 25A and 25B, show an exemplary depiction of the visual display in a smartphone device for angular navigation in CT in-axial plane targeting is shown. As shown in FIG. 25A, image 40 shows instrument 20 and instrument tracker 100. In the illustrated exemplary image instrument 20 and instrument tracker 100 are shown in a CT image of a needle instrument and instrument tracker in a CT in-axial-plane view acquired with an imaging device. FIG. 25B shown the angular orientation of instrument 20 on display unit 26, which in illustrated exemplary embodiment is a smartphone display running a smartphone application.

The methods and systems of the present disclosure, as described above and shown in the drawings, provide for instrument trackers, instrument tracking systems, and methods tracking position of an instrument along an insertion path within a subject with superior properties including real-time positional awareness by fusing image data with positional and or angular orientation information. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. An instrument tracker, comprising:
   a case having an interior and an exterior, wherein a plurality of structures are arranged on the exterior of the case and define an instrument channel;
   an inertial measurement unit (IMU) arranged within the interior of the case, wherein the IMU includes: one or more of a magnetometer, an accelerometer, or a gyroscope; and a gravity sensor configured to identify a gravity vector;
   a controller arranged within the interior of the case and disposed in communication with the IMU; and
   a memory disposed in communication with the controller, the memory having a non-transitory machine readable medium with instructions recorded thereon that, when read by the controller, cause the controller to:

calibrate the instrument tracker for off-axial plane angles by generating one or more calibration matrices;

subsequent to calibrating the instrument tracker, receive at least one of positional and orientation information from the IMU;

determine a position and an orientation of an instrument fixed relative to the case within the instrument channel using the positional and orientation information received from the IMU; and transmit the position and the orientation of the instrument to an output device for providing feedback related to the position and the orientation of the instrument relative to a predetermined insertion path through a subject between an entry point on a surface of the subject and a region of interest within an interior of the subject, wherein, in response to the predetermined insertion path corresponding to an in-axial plane angle of an imaging device, the controller adjusts the orientation information for two axes of the instrument tracker based on the gravity vector without using the one or more calibration matrices; and wherein, in response to the predetermined insertion path corresponding to an off-axial plane angle of the imaging device that is different from the in-axial plane angle, the controller adjusts the orientation information for the two axes based on the one or more calibration matrices generated during calibration of the instrument tracker, wherein the one or more calibration matrices align the two axes to the imaging device.

2. The instrument tracker as recited in claim 1, wherein the case comprises four supports arranged on the interior of the case to support the IMU.

3. The instrument tracker as recited in claim 1, wherein the case includes a grip with a finger seat disposed on the exterior of the case, the finger seat disposed on a side of the case opposite the plurality of structures that define the instrument channel.

4. The instrument tracker as recited in claim 1, wherein the case includes a finger ring disposed on the exterior of the case.

5. The instrument tracker as recited in claim 1, further comprising a battery arranged within the interior of the case and electrically connected to the IMU and the controller.

6. The instrument tracker as recited in claim 5, further comprising a wired charging circuit electrically connected to the battery.

7. The instrument tracker as recited in claim 5, further comprising a wireless charging circuit electrically connected to the battery.

8. The instrument tracker as recited in claim 1, further comprising a wireless communication module, the controller operatively connected to the wireless communication module.

9. The instrument tracker as recited in claim 1, wherein the instrument includes at least one of a needle, a catheter, or a portable imaging device.

10. The instrument tracker as recited in claim 1, further comprising a tracker user interface fixed relative to the case, wherein the controller is operatively connected to the tracker user interface.

11. The instrument tracker as recited in claim 10, wherein the tracker user interface includes at least one of an auditory module or a display module.

12. The instrument tracker as recited in claim 1, wherein the region of interest includes an anatomical target of the subject undergoing an intervention procedure.

13. The instrument tracker as recited in claim 1, wherein the output device comprises a display device controller configured to:

receive image data of the subject including the region of interest;

define the predetermined insertion path extending between the entry point and the region of interest;

receive data from the instrument tracker indicative of at least one of the orientation and an insertion depth of the instrument;

compare the at least one of the orientation and the insertion depth of the instrument to the predetermined insertion path; and display the at least one of the orientation and the insertion depth relative to the insertion path.

14. An instrument tracking system, comprising:

an instrument tracker as recited in claim 1, further comprising a wireless communication module disposed within the case, the controller operatively connected to the wireless communication module for communicating at least one of the orientation and an insertion depth of the instrument to the output device wirelessly; and the output device, wherein the output device includes a display device controller disposed in communication with a memory having instructions recorded on the memory that, when read by the display device controller, cause the display device controller to:

receive image data of the subject including the region of interest;

define the predetermined insertion path extending between the entry point and the region of interest;

receive data from the instrument tracker indicative of at least one of the orientation and an insertion depth of the instrument;

compare the at least one of the orientation and the insertion depth of the instrument to the predetermined insertion path; and display the at least one of the orientation and the insertion depth of the instrument relative to the predetermined insertion path.

15. The instrument tracking system as recited in claim 14, further comprising the imaging device, wherein the imaging device is at least one of an x-ray imaging device, a computerized tomography device, a positron emission tomography imaging device, a magnetic resonance imaging device, or an ultrasound imaging device for capturing the image data, wherein each of the x-ray imaging device, the computerized tomography device, the positron emission tomography imaging device, the magnetic resonance imaging device, or the ultrasound imaging device are disposed in communication with the output device.

16. A method of tracking a position of an instrument, the method comprising:

calibrating an instrument tracker for off-axial plane angles by generating one or more calibration matrices;

fixing the instrument tracker to the instrument, the instrument tracker including a case having an interior and an exterior, an inertial measurement unit (IMU) arranged within the interior of the case, the IMU including at least a gravity sensor configured to identify a gravity vector, and a controller arranged within the interior of the case and disposed in communication with the IMU, wherein the IMU further includes one or more of a magnetometer, an accelerometer, or a gyroscope;

subsequent to calibrating the instrument tracker, receiving at least one of positional and orientation information from the IMU;

determining a position and an orientation of the instrument using the positional and orientation information received from the IMU;

transmitting the position and the orientation of the instrument to a display device disposed in communication with the instrument tracker;

comparing the position and the orientation of the instrument to a predetermined insertion path defined between an entry point located on a surface of a subject and a region of interest located within the subject; and calculating a difference between the orientation and an insertion depth of the instrument and the insertion path to provide feedback about the difference via an output device, wherein the feedback comprises at least one of an image generated from in-axial plane image data captured using an imaging device or audio feedback, wherein, in response to the predetermined insertion path corresponding to an in-axial plane angle of the imaging device, the controller adjusts the orientation information for two axes of the instrument tracker based on the gravity vector without using the one or more calibration matrices; and wherein, in response to the predetermined insertion path corresponding to an off-axial plane angle of the imaging device that is different from the in-axial plane angle, the controller adjusts the orientation information for the two axes based on the one or more calibration matrices generated during calibration of the instrument tracker, wherein the one or more calibration matrices align the two axes to the imaging device.

17. The method as recited in claim 16, further comprising:

imaging the subject including the region of interest located within the subject;

determining the predetermined insertion path using imaging data acquired during the imaging of the subject including the region of interest; and confirming the position of the instrument by imaging the instrument and subject including the region of interest subsequent to completion of insertion of the instrument along the predetermined insertion path.

* * * * *